(12) United States Patent
Solotoff

(10) Patent No.: US 11,839,243 B1
(45) Date of Patent: Dec. 12, 2023

(54) THERAPEUTIC SHIRT WITH HIGH COMPRESSION SUPPORT FOR IMPROVED POSTURE FOR PREGNANT WOMEN AND OVERWEIGHT WEARERS

(71) Applicant: PREFERRED PRESCRIPTION, INC., Hollywood, FL (US)

(72) Inventor: Brandon Solotoff, Boca Raton, FL (US)

(73) Assignee: Preferred Prescription, INC., Hollywood, FL (US)

( * ) Notice: Subject to any disclaimer, the term of this patent is extended or adjusted under 35 U.S.C. 154(b) by 1 day.

(21) Appl. No.: 17/008,734

(22) Filed: Sep. 1, 2020

Related U.S. Application Data

(60) Provisional application No. 62/899,277, filed on Sep. 12, 2019.

(51) Int. Cl.
*A41D 13/05* (2006.01)
*A41B 1/08* (2006.01)
(Continued)

(52) U.S. Cl.
CPC ............ *A41D 13/0531* (2013.01); *A41B 1/08* (2013.01); *A61F 5/02* (2013.01); *A41D 13/0002* (2013.01)

(58) Field of Classification Search
CPC ............ A41D 13/0531; A41D 13/0002; A41D 2400/38; A41D 13/00; A41B 1/08; A41C 1/08; A41C 1/02; A61F 5/02
See application file for complete search history.

(56) References Cited

U.S. PATENT DOCUMENTS

| 114,615 A | 5/1871 | Smitley |
| 2,403,676 A | 7/1946 | Modlinski |

(Continued)

FOREIGN PATENT DOCUMENTS

| CA | 2838790 | 12/2012 |
| EP | 2430931 | 3/2012 |

(Continued)

OTHER PUBLICATIONS

"Study of Properties of Medical Compression Fabrics," Lijing Wang, et al., Journal of Fiber Bioengineering & Informatics, Global Science Press, p. 15-22 (2011).

(Continued)

*Primary Examiner* — Heather Mangine
*Assistant Examiner* — Raquel M. Weis
(74) *Attorney, Agent, or Firm* — Thomas A. O'Rourke; James Bongiorno

(57) ABSTRACT

A posture support garment includes: a shirt, shoulder band, and waist band. The shirt envelops the wearer's torso and shoulders, and is an elastic material configured to apply a first level of compression. The shoulder band is fixedly secured to the shirt to encircle the left and right shoulders of the shirt and crisscross at a back region, and is made of a first compression material configured to apply a second level of compression. The waist band is formed with a first portion that extends around the back of the wearer's waist and is made of the first compression material to apply the second level of compression, and a second portion that extends around the front of the wearer's waist, and is made of a second compression material configured to apply a third level of compression, where the third level of compression is less than the second level of compression.

11 Claims, 18 Drawing Sheets

(51) Int. Cl.
*A61F 5/02* (2006.01)
*A41D 13/00* (2006.01)

(56) References Cited

U.S. PATENT DOCUMENTS

| | | | |
|---|---|---|---|
| 3,008,468 A * | 11/1961 | Helene | A41C 3/00 |
| | | | 450/86 |
| 3,338,236 A | 8/1967 | McLeod | |
| 3,476,102 A | 11/1969 | Sarnoff | |
| 3,950,789 A | 4/1976 | Konz | |
| 4,384,369 A | 5/1983 | Prince | |
| 4,480,637 A | 11/1984 | Florek | |
| 4,698,847 A * | 10/1987 | Yoshihara | A41C 1/06 |
| | | | 450/7 |
| 4,789,372 A * | 12/1988 | Wicks | A41C 1/10 |
| | | | 2/908 |
| 5,038,779 A | 8/1991 | Barry | |
| 5,109,546 A * | 5/1992 | Dicker | A41D 13/0015 |
| | | | 482/121 |
| 5,302,806 A | 4/1994 | Simmons | |
| 5,536,246 A | 7/1996 | Saunder | |
| 5,555,566 A | 9/1996 | Kuhn | |
| 5,628,725 A | 5/1997 | Ostergard | |
| 5,826,273 A | 10/1998 | Eckes | |
| 5,857,990 A | 1/1999 | Maas | |
| 5,915,531 A * | 6/1999 | Hilpert | A41D 1/21 |
| | | | 450/155 |
| 5,937,442 A * | 8/1999 | Yamaguchi | A41D 31/18 |
| | | | 2/69 |
| 6,176,816 B1 * | 1/2001 | Dicker | A63B 21/4009 |
| | | | 2/69.5 |
| 6,306,111 B1 | 10/2001 | Dean | |
| 6,440,094 B1 * | 8/2002 | Maas | A61F 5/3746 |
| | | | 602/5 |
| 6,709,411 B1 | 3/2004 | Olinger | |
| 7,134,969 B2 * | 11/2006 | Citron | A61F 5/026 |
| | | | 602/5 |
| 7,246,381 B2 | 7/2007 | Green | |
| 7,871,388 B2 * | 1/2011 | Brown | A61F 5/3746 |
| | | | 602/19 |
| 7,908,670 B2 * | 3/2011 | Semba | A41D 1/04 |
| | | | 2/69 |
| 8,047,893 B2 * | 11/2011 | Fenske | A41F 15/002 |
| | | | 450/86 |
| 8,113,911 B1 * | 2/2012 | Hansen | A41D 1/21 |
| | | | 450/86 |
| 8,172,782 B2 | 5/2012 | Rock | |
| 8,214,926 B2 | 7/2012 | Brown | |
| 8,220,074 B2 * | 7/2012 | Sutker | A41D 13/0058 |
| | | | 2/69 |
| 8,235,766 B2 * | 8/2012 | Melarti | A41C 1/06 |
| | | | 450/96 |
| 8,256,034 B2 | 9/2012 | Berner | |
| 8,286,262 B2 * | 10/2012 | Rance | A41D 7/00 |
| | | | 2/69 |
| 8,434,163 B1 | 5/2013 | Nudo | |
| 8,533,864 B1 * | 9/2013 | Kostrzewski | A41D 13/0015 |
| | | | 2/69 |
| 8,597,222 B2 | 12/2013 | Lucero | |
| 8,827,767 B2 * | 9/2014 | Samoodi | A41C 1/10 |
| | | | 450/20 |
| 8,876,875 B1 | 11/2014 | Nilforushan | |
| 8,905,956 B2 * | 12/2014 | Waeger | A61F 5/026 |
| | | | 128/846 |
| 8,910,317 B2 * | 12/2014 | Decker | A41D 31/185 |
| | | | 602/19 |
| 9,009,863 B2 * | 4/2015 | Decker | A41D 31/185 |
| | | | 2/45 |
| 9,167,854 B2 * | 10/2015 | Levian | A41B 1/08 |
| 9,226,534 B2 * | 1/2016 | Puni | A41B 1/08 |
| 9,339,065 B2 | 5/2016 | Willis | |
| 9,370,440 B2 * | 6/2016 | Ingimundarson | A61F 5/028 |
| 9,439,459 B2 * | 9/2016 | Placanica | A41D 13/0007 |
| 9,452,078 B2 * | 9/2016 | Waeger | A61F 5/026 |
| 9,534,324 B2 * | 1/2017 | Lonati | D04B 15/58 |
| 9,572,705 B2 | 2/2017 | Ingimundarson | |
| 9,598,794 B2 | 3/2017 | Isanhart | |
| D793,570 S | 8/2017 | Sherman | |
| 9,883,703 B2 * | 2/2018 | Schultz | A41D 1/00 |
| 10,264,828 B2 | 4/2019 | Brown | A41C 3/0057 |
| 10,357,067 B2 * | 7/2019 | Yeomans | A41D 13/02 |
| 10,376,404 B2 * | 8/2019 | Webster | A61F 5/0118 |
| 2005/0177920 A1 * | 8/2005 | Wilkinson | A41F 9/025 |
| | | | 2/69 |
| 2006/0218692 A1 | 10/2006 | Lamarque | |
| 2007/0149093 A1 * | 6/2007 | Lutz | A41C 3/00 |
| | | | 450/1 |
| 2007/0299489 A1 | 12/2007 | Francis | |
| 2008/0125842 A1 * | 5/2008 | Petitt | A61F 7/02 |
| | | | 607/108 |
| 2008/0195010 A1 * | 8/2008 | Lai | A63B 23/0244 |
| | | | 602/5 |
| 2008/0208089 A1 | 8/2008 | Newkirk | |
| 2009/0062704 A1 * | 3/2009 | Brown | A61F 5/026 |
| | | | 602/19 |
| 2009/0270012 A1 * | 10/2009 | Melarti | A41C 3/08 |
| | | | 450/11 |
| 2011/0214216 A1 * | 9/2011 | Zarabi | A41F 9/00 |
| | | | 2/69 |
| 2011/0302686 A1 * | 12/2011 | Chapuis | A41D 13/0015 |
| | | | 2/242 |
| 2012/0059297 A1 * | 3/2012 | Newkirk | A61F 5/026 |
| | | | 602/19 |
| 2012/0078147 A1 * | 3/2012 | Ogulnick | A61F 13/143 |
| | | | 602/2 |
| 2012/0129425 A1 * | 5/2012 | Bevans | A41D 1/06 |
| | | | 450/11 |
| 2012/0156962 A1 * | 6/2012 | Krawchuk | A41C 1/00 |
| | | | 450/156 |
| 2012/0174282 A1 * | 7/2012 | Newton | A41D 31/185 |
| | | | 2/69 |
| 2012/0316483 A1 * | 12/2012 | Waeger | A61F 5/026 |
| | | | 602/19 |
| 2013/0047312 A1 * | 2/2013 | Wilson | A41D 13/0012 |
| | | | 2/69 |
| 2013/0104280 A1 * | 5/2013 | Boynton | A61F 5/026 |
| | | | 2/69 |
| 2014/0238085 A1 * | 8/2014 | Smith | A61F 13/08 |
| | | | 66/175 |
| 2014/0317826 A1 * | 10/2014 | Decker | A41D 13/0015 |
| | | | 2/69 |
| 2014/0336544 A1 | 11/2014 | Ransom | |
| 2014/0336556 A1 * | 11/2014 | Pucik | A61F 5/02 |
| | | | 602/19 |
| 2015/0264980 A1 * | 9/2015 | Tally | A63B 21/4011 |
| | | | 2/69 |
| 2015/0264981 A1 * | 9/2015 | Solano | A41B 11/00 |
| | | | 450/99 |
| 2015/0335472 A1 | 11/2015 | Li | |
| 2016/0015088 A1 * | 1/2016 | Hendrickson | A41D 1/21 |
| | | | 450/95 |
| 2016/0249698 A1 * | 9/2016 | Berzowska | A41D 13/1281 |
| | | | 2/69 |
| 2016/0255883 A1 * | 9/2016 | Morag | A41D 13/0015 |
| 2016/0278963 A1 * | 9/2016 | Webster | A61F 5/05858 |
| 2017/0013886 A1 * | 1/2017 | Towfigh | A41C 1/08 |
| 2017/0027240 A1 * | 2/2017 | McClean | A41D 1/14 |
| 2017/0071264 A1 * | 3/2017 | Towfigh | A41C 1/10 |
| 2017/0231798 A1 * | 8/2017 | Shin | A41D 31/18 |
| | | | 2/44 |
| 2018/0295892 A1 * | 10/2018 | Caden | A41C 1/10 |
| 2018/0317562 A1 * | 11/2018 | Gagliardo | A41B 1/08 |
| 2019/0000159 A1 | 1/2019 | Roberts | |
| 2019/0045855 A1 * | 2/2019 | Musciacchio | A41D 7/005 |
| 2019/0059462 A1 * | 2/2019 | Grogro | A41D 13/0007 |
| 2019/0246717 A1 * | 8/2019 | Fischer | A41D 27/00 |

(56) References Cited

U.S. PATENT DOCUMENTS

2019/0320738 A1* 10/2019 Kiuchi .................. A41D 1/215
2019/0380408 A1* 12/2019 Tanzman ................ A61F 5/026

FOREIGN PATENT DOCUMENTS

EP          3315103      5/2018
GB          2504313      1/2014

OTHER PUBLICATIONS

"Compression Garments for Medical Therapy and Sports," Ying Xiong and Xiaoming Tao, Polymers, vol. 10, No. 663, 3-19, Jun. 14, 2018.
"From 3d Scan to Body Pressure of Compression Garments," Li Z, Malengier B, et al., AUTEX2019—19th World Textile Conf. on Textiles at the Crossroads, Jun. 11-15, 2019.
"Physics of Compression," Hugo Partsch, Published by Guset User, Nov. 24, 2015.
Bringing Light Into the Dark: Effects of Compression Clothing on Performance and Recovery, Dennis-Peter Born, International Journal of Sports Physiology and Performance, 2013.

* cited by examiner

THERAPEUTIC SHIRT WITH HIGH COMPRESSION SUPPORT FOR IMPROVED POSTURE FOR PREGNANT WOMEN AND OVERWEIGHT WEARERS

CROSS REFERENCES TO RELATED APPLICATIONS

This application claims priority on U.S. Provisional Application Ser. No. 62/899,277, filed on Sep. 12, 2019, the disclosures of which are incorporated herein by reference.

FIELD OF THE INVENTION

The subject technology relates generally to compression garments, and more particularly to a compression garment configured with specially located high compression regions to provide improved posture support particularly for pregnant and overweight wearers.

BACKGROUND OF THE INVENTION

Compression garments are clothing items that may be worn to provide support in the form of compressive pressure applied to a particular region or regions of the wearer's body. Compression garments may be used by the wearer for therapeutic reasons and also for enhancing an athlete's performance during sporting events. In general, the use of various different pressures that may be achieved by compression fabrics with different engineered compression gradients for medical purposes has been studied. See e.g., "Study of Properties of Medical Compression Fabrics," LIJING WANG, MARTIN FELDER, and JACKIE Y. CAI, Journal of Fiber Bioengineering & Informatics, Global Science Press, p. 15-22 (2011); "Compression Garments for Medical Therapy and Sports," YING XIONG and XIAOMING TAO, Polymers, Vol. 10, No. 663, 3-19, Jun. 14, 2018; "From 3d Scan To Body Pressure Of Compression Garments," LI Z, MALENGIER B, VASILE S, COOLS J, VAN LANGENHOVE L, AUTEX2019-19th World Textile Conference on Textiles at the Crossroads, 11-15 Jun. 2019, Ghent, Belgium; "Physics of Compression," HUGO PARTSCH, Published by Guset User, 2015-11-24; and "Bringing Light Into the Dark: Effects of Compression Clothing on Performance and Recovery," Dennis-Peter Born, Billy Sperlich, and Hans-Christer Holmberg, International Journal of Sports Physiology and Performance, 8:4-18 (2013).

Examples of the use of compression garments for medical reasons include compression stockings for improving blood circulation, and treating varicose veins, edema, lymphedema, and deep vein thrombosis. Compression socks may be worn on a plane where a person is inactive and confined in a small space to reduce the risk of blood clots. Compression stockings and socks may also be worn by a person who must stand for long periods of time. Compression sleeves may also be worn on a person's legs to treat shin splints, muscle cramps, and tendonitis.

With respect to the compression garments being used to enhance athletic performance, such use helps the muscles to more quickly recover from previous strenuous activity. Scientific studies have shown that the wearing of a compression sleeve causes the walls of the wearer's arteries to dilate, thereby increasing the flow of blood to those muscles, and providing more oxygen and nutrients needed, which also tends to reduce the build-up of lactic acid. The wearing of a compression sleeve may also serve to support the muscles and reduce muscular vibrations, reducing the fatigue that results from those vibrations, thereby improving athletic endurance.

The typical compression stockings are formed to provide graduated compression, whereby maximum compression is provided at the ankle, with decreasing compression being provided in moving along the stocking upwardly in the direction towards the knee and hip.

One problem with many prior art devices is that they include straps that are unnecessarily confining and very uncomfortable, and many are very unsightly, and typically cannot be worn without being seen because they are intended to be worn over the person's clothing.

Some garments for enhancing various aspect of the wearer (e.g., proper posture) may include, for example, the following U.S. Pat. No. 5,937,442 to Yamaguchi; U.S. Pat. No. 6,440,094 to Maas; U.S. Pat. No. 7,871,388 to Brown; U.S. Pat. No. 8,172,782 to Rock, U.S. Pat. No. 8,827,767 to Samoodi; U.S. Pat. No. 9,167,854 to Levian; 2009/0062704 (Brown); and 2012/0078147 Ogulnick.

A therapeutic shirt that provides targeted support to improve the posture of a pregnant woman and an overweight wearer is disclosed herein.

The therapeutic shirt disclosed herein provides improvements with respect to the support provided to the shoulders and the spine, and the comfort when worn by the person, which is incredibly important for a pregnant woman who already experiences higher than normal levels of discomfort while carrying a baby in utero. The therapeutic shirt disclosed herein may also be worn beneath a regular shirt that the user may typically wear on a causal evening out.

It is noted that citing herein of any patents, published patent applications, and non-patent literature is not an admission as to any of those references constituting prior art with respect to the herein disclosed apparatus.

OBJECTS OF THE INVENTION

It is an object of the invention to provide a compression garment in the form of a shirt that may be worn to improve the posture of a pregnant woman.

It is another object of the invention to provide a compression garment in the form of a shirt that may be worn to improve the posture of an overweight wearer.

It is a further object of the invention to provide a compression garment in the form of a shirt that may be worn to improve the posture of a person who sits all day long.

It is another object of the invention to provide a compression garment in the form of a shirt that may be worn to improve the posture of a person who works in a labor intensive job, such as construction workers, or moving company workers.

It is also an object of the invention to provide a compression garment in the form of a shirt that may be configured to pull the shoulders of the wearer back to improve posture and allow for easier breathing, by increasing lung capacity.

It is another object of the invention to provide a compression garment in the form of a shirt that may be configured to reduce the mid-back stress of a pregnant woman due to her breasts becoming enlarged.

It is also an object of the invention to provide a compression garment in the form of a shirt that may be configured to reduce low back compression and lumbar spinal stenosis.

It is another object of the invention to provide a compression garment that combines a plurality of fabric segments having differing elastic properties to form a compression garment having regions of differential compression that are particularly configured to enhance the support provided to the wearer.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with at least one embodiment, a posture support garment for improving the posture of a wearer may include: a shirt, a shoulder band, and a waist band. The shirt is configured to envelop at least a portion of the wearer's torso and the wearer's shoulders, and the shirt may be formed of an elastic material configured to apply a first level of compression. The shoulder band is fixedly secured to the shirt and configured to encircle a left shoulder and a right shoulder of the shirt in a particular manner such that: the shoulder band crosses over a right shoulder region of the shirt, travels down a right chest region of the shirt and curves back around a right side of the shirt and traverses across a back of the shirt upwardly towards a left shoulder region, and travels down a left chest region of the shirt and around a left side of the shirt and traverses across the back of the shirt upwardly towards the right shoulder region, crisscrossing at a central portion of the back of the shirt. The shoulder band is formed of a first compression material configured to apply a second level of compression. The waist band is configured to encircle the wearer's waist, and includes a first portion and a second portion formed into a circumferential band. The second portion of the waist band is configured to extend around the front of the wearer's waist and is formed of a second compression material configured to apply a third level of compression. The first portion of the waist band is configured to extend around the back of the wearer's waist and is also formed of the first compression material being configured to apply the second level of compression. The third level of compression is less than the second level of compression. Each of the first compression material and the second compression material may be formed of three layers of material being an innermost layer, a middle layer, and an outermost layer.

When the garment is used for improving the posture of a pregnant wearer, the first compression material of the waist band may be formed of a high compression material, and the second compression material of the waist band may be formed of a low compression material. When the garment is used for improving the posture of an overweight wearer, the first compression material may be formed of a high compression material, and the second compression material may be formed of a medium compression material. The low, medium, and high compression materials may be formed of a plurality of layers of material including, but not limited to, thermoplastic elastomer (TPE), or a polyurethane. The shirt may be formed of a single layer of elastic material including, but not limited to, a spandex, a polyester blend, and a bamboo blend.

The posture support garment may also include a first pocket and a second pocket formed on the back of the shirt. Each of the first pocket and the second pocket may be formed with a respective opening that is positioned on the back above the waistband. Each of the first and second pockets may be formed outside of the outermost most layer of the high compression material, or may be formed beneath the innermost layer of the high compression material, or may be formed between the innermost layer and the middle layer of the high compression material, or may be formed between the middle layer and the outermost layer of the high compression material.

BRIEF DESCRIPTION OF THE DRAWINGS

The description of the various example embodiments is explained in conjunction with appended drawings, in which.

DETAILED DESCRIPTION OF THE INVENTION

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

It is further noted that any use herein of relative terms such as "top," "bottom," "upper," "lower," "vertical," and "horizontal" are merely intended to be descriptive for the reader, and may be based on the depiction of those features within the figures for one particular position of the garment, and such terms are not intended to limit the orientation with which the disclosed garment may be oriented/utilized.

Figures 6A, 6B:
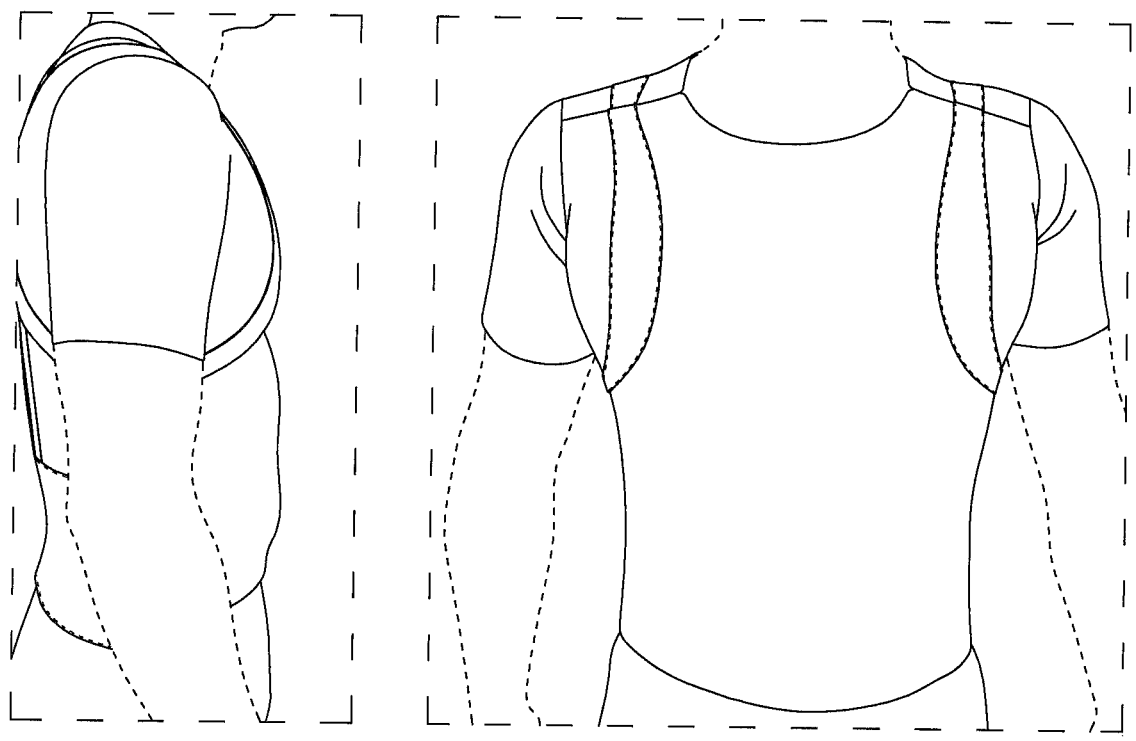
FIGS. 6A-6C are side and front views of the therapeutic shirt of FIGS. 1-2, shown after being donned by a person, and being shown in FIG. 6C while the person is bending over with his/her arms extended away from the torso.
Figure 6C:
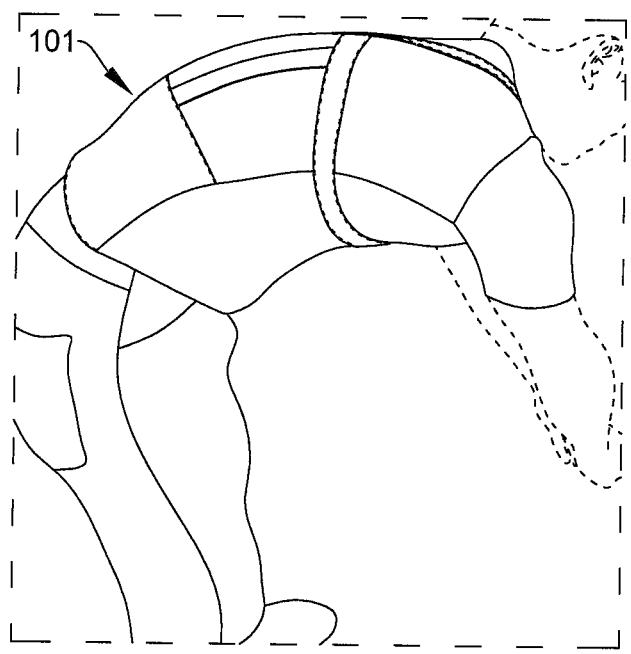
Figures 7A, 7B:
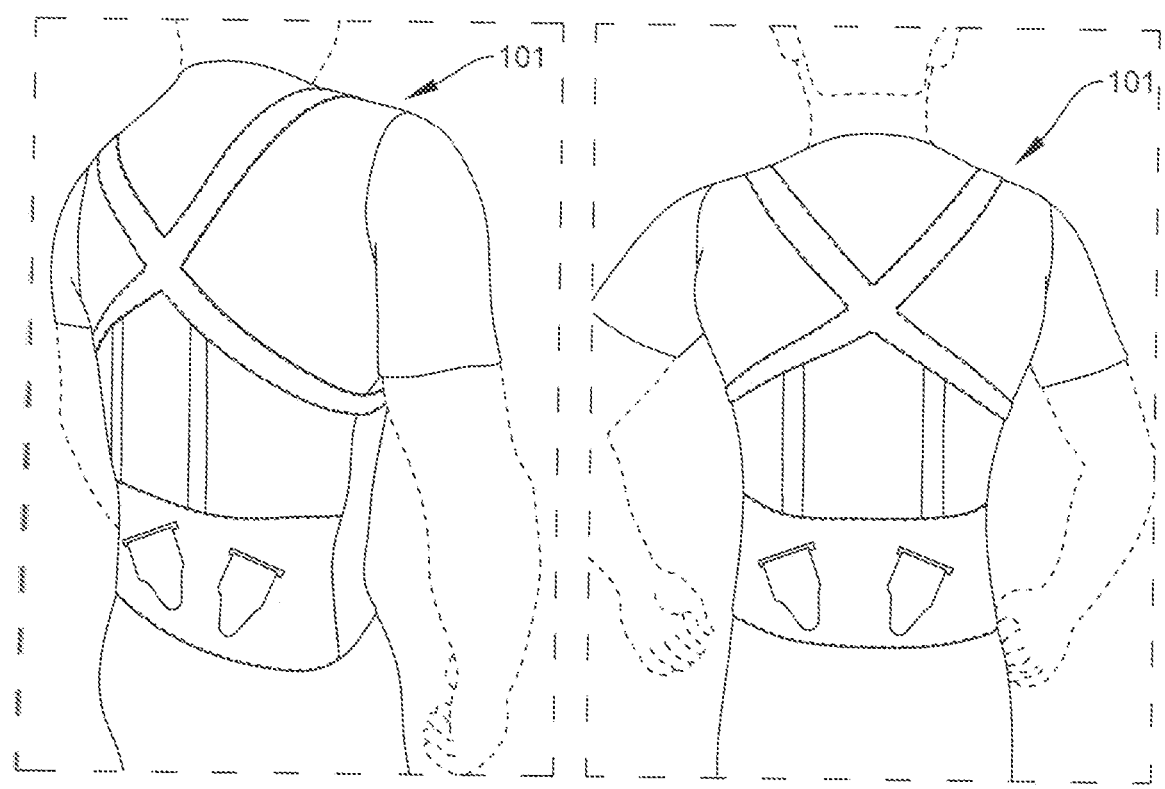
FIGS. 7A-7B are views of an alternate version of the therapeutic shirt of FIG. 1 that is the same as the embodiment shown in FIGS. 1-2, except that it includes pockets on the back side, and is shown therein after being donned by a person.
Figure 8:
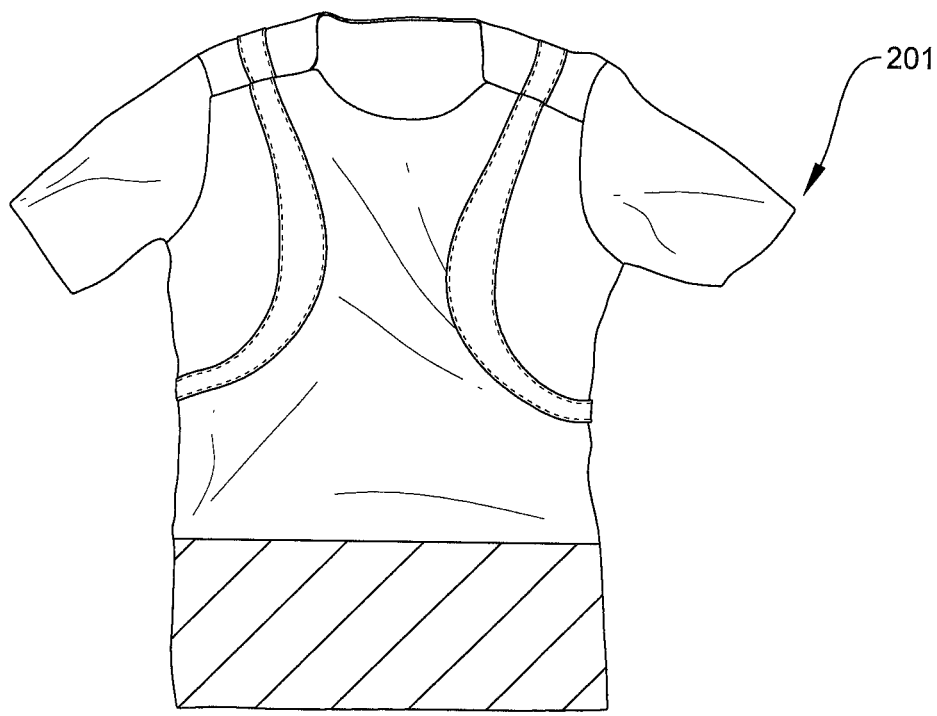
FIG. 8 is a front view of a second embodiment of a therapeutic shirt with high compression support for improved posture for pregnant women and overweight wearers.

FIGS. 1-4 illustrate views of a first embodiment of a compression garment in the form of a collarless therapeutic shirt 101 that has specially located high compression material to provide support to improve the posture of a pregnant woman and/or an overweight wearer. FIGS. 6A-6C illustrate the therapeutic shirt 101 after being donned by a person.

Figure 1:
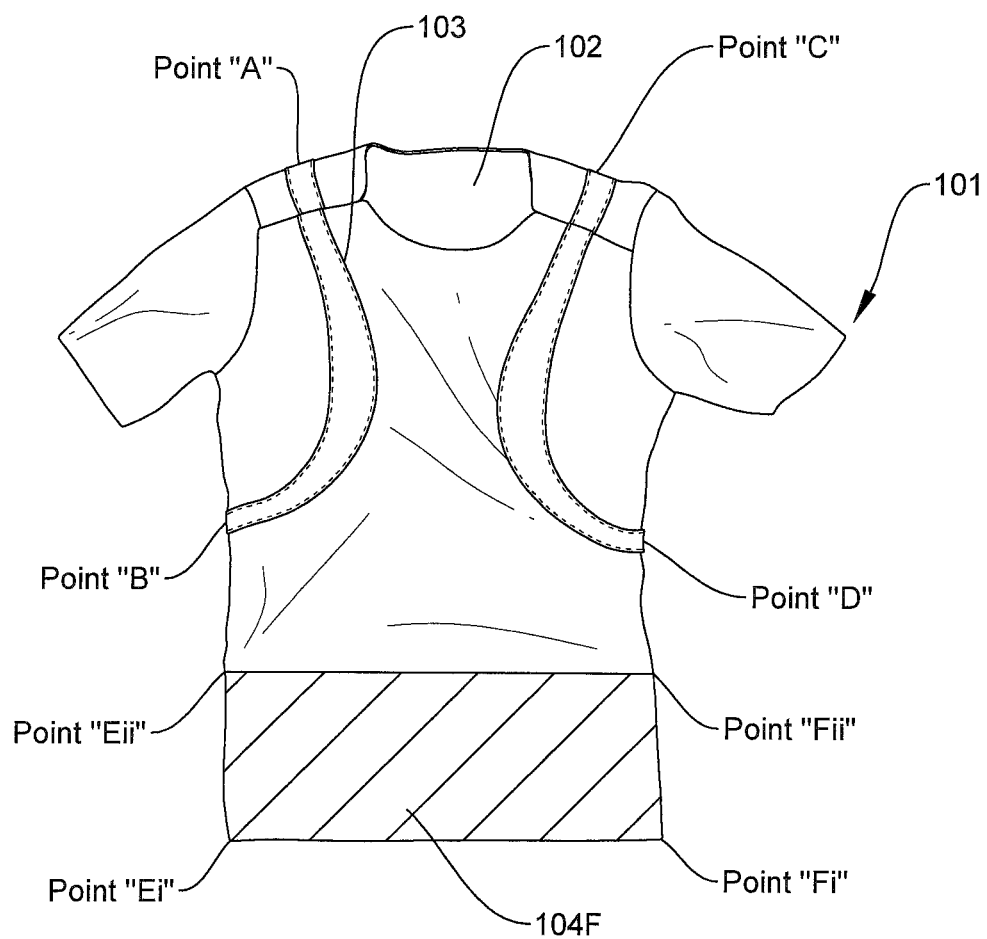
FIG. 1 is a front view of a therapeutic shirt with high compression support for improved posture for pregnant women and overweight wearers.
Figure 2:
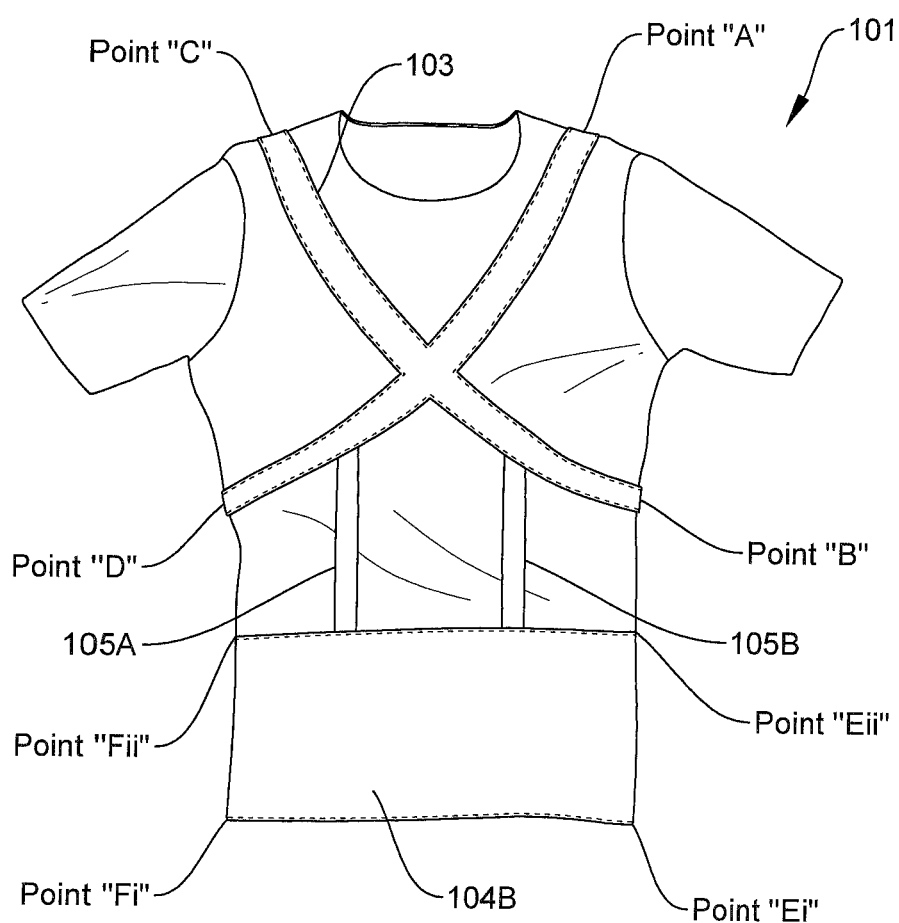
FIG. 2 is a rear view of the therapeutic shirt shown in FIG. 1.
Figure 3:
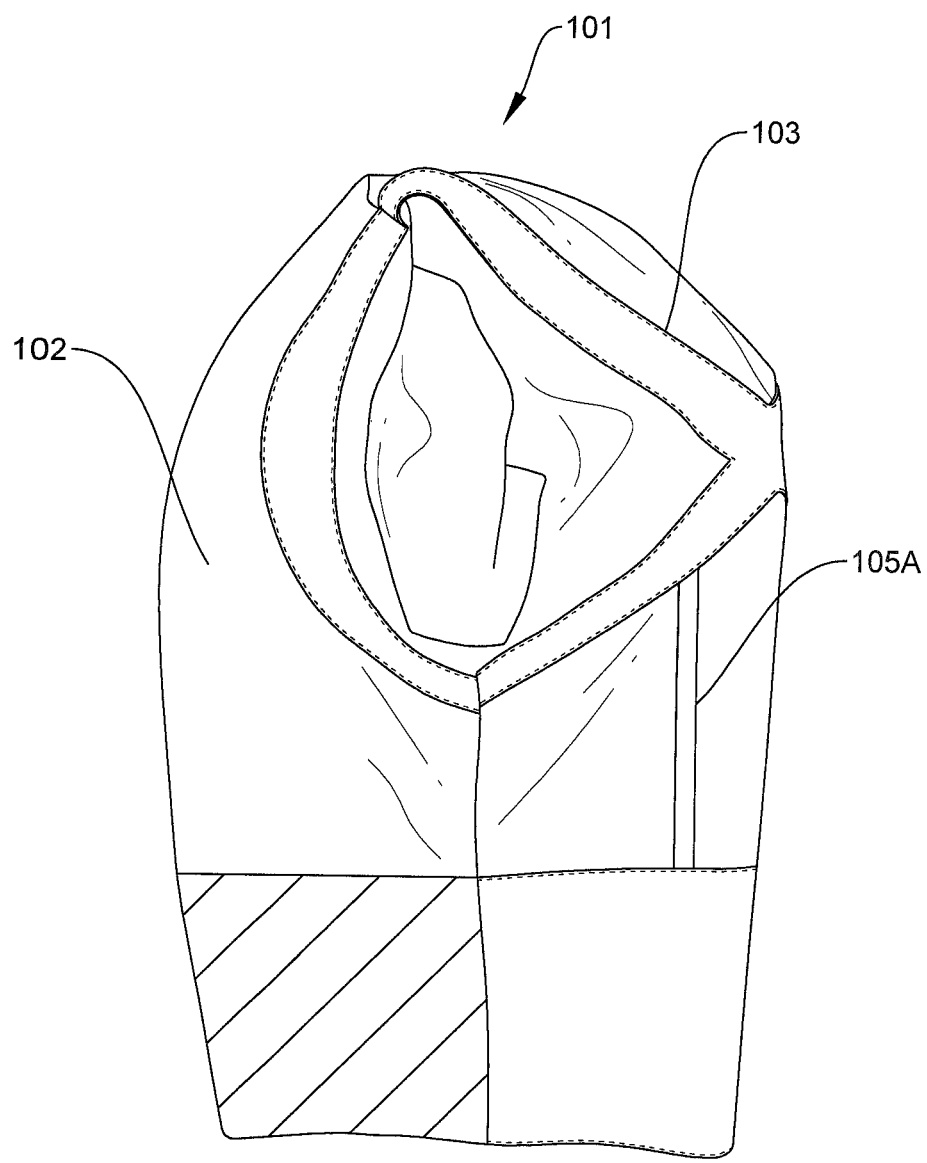
FIG. 3 is a side view of the therapeutic shirt shown in FIG. 1.
Figure 4:
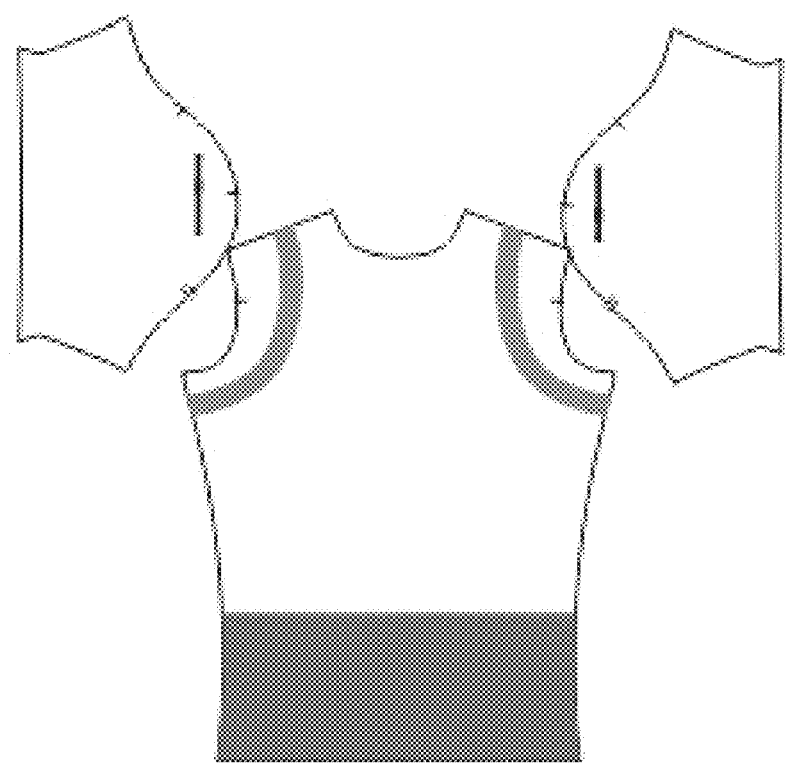
FIG. 4 and FIG. 5 are views of the flat patterns for the front side and sleeves, and for the rear side of the therapeutic shirt of FIG. 1.
Figure 5:
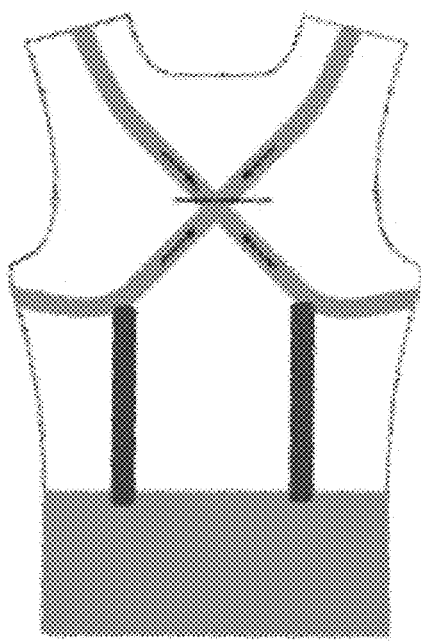

As seen in FIG. 1 and FIG. 2, the therapeutic shirt 101, which may be substantially symmetrical, may include a base shirt 102 formed of slightly elastic material 102, which is shown in the light/white color. The material of the base shirt 102 may be a two-way stretch fabric, but is more preferably a four-way stretch fabric (i.e., it can stretch in both directions-cross-wise and lengthwise), and may be a single layer or multiple layers of any suitable stretch material known in the art, including, but is not limited to, spandex, a polyester blend, a bamboo blend, etc. The base shirt 102 preferably is sized and has sufficient elasticity to substantially conform to the body contours of the wearer, as shown for example in FIGS. 6A-6C and FIGS. 7A-7B. At least several different sizes for the base shirt 102 may preferably be utilized and constructed as described hereinafter to suitably fit a range of different sized wearers, and to apply compression in the desired ranges.

To provide support to enhance the posture of the wearer, low, medium, and/or high compression materials may be attached at several select locations of the elastic base shirt 102, and in any suitable manner known in the art, including, but not limited to, being stitched thereto. Alternatively, the medium and/or high compression materials may replace the stretch fabric of the base shirt 102 where those materials are utilized. The low, medium, and high compression materials may be foil led of multiple layers of material, and at least one layer may be a mesh. Each of the layers of the low, medium, and high compression materials may be made of any suitable material known in the art, including, but not limited to, a thermoplastic elastomer (TPE), and a polyurethane, which may also be layered with spandex. In one embodiment, each of the medium and the high compression materials may be formed of three layers of material—an innermost layer that contacts the skin of the wearer, a middle layer, and an outermost layer that is visible, with at least the middle layer being formed of a mesh.

The low/medium/high compression material may be applied to the base shirt as follows.

First, a shoulder band 103 of high compression material shown in the darker color may circle from the front to the back of the shirt 102, and then from the back to the front of the shirt, as follows: the band 103 of high compression material may cross over the right shoulder at point "A", travel down the right side of the chest and curve backwardly around the right side of the shirt at point "B"; and after crossing the side at point "B" the band traverses across the back of the shirt upwardly towards the left shoulder, and upon reaching point C on the left shoulder the band travels down the left front side of the chest and curves backwardly around the side of the shirt at point "D" and subsequently traverses across the back of the shirt upwardly towards the right shoulder to return back to point "A," crisscrossing over itself on the back side. Thus the band 103 may be one continuous member, or instead may be formed of a series of smaller band portions that area fixedly secured together, along with attachment to the base shirt 102. The band 103 being so secured to the base shirt 102 may serve, when the therapeutic shirt 101 is being worn, pull the anterior aspect of the shoulders back and limit forward should movements to improve posture and open the wearer's airway/lungs to allow for easier breathing.

Second, a compression band may be formed at the waist of the base shirt 102. In various embodiments, the compression band formed at the waist may be a single wide continuous band made of the same material, or it may be a plurality of waist bands of the same material, or it may be a single wide band where portions may be made up of different materials, or it may be a plurality of band portions which may be made up of the same or different compression materials. In the embodiments where different materials are used for the waist band, as seen for example for therapeutic shirt 101 in FIG. 1 and FIG. 2 and for therapeutic shirt 301 in FIG. 13 and FIG. 14, the waist band may be formed to have a first portion and a second portion, where for shirt 101 the first portion 104B (see FIG. 2) extends around the back of the wearer's waist, and the second portion 104F (see FIG. 1) extends around the front of the wearer's waist. The respective ends of each of the first portion 104B of the waist band and the second portion 104F may be secured to each other at the two sides of the base shirt 102, e.g., between points "Ei" to "Eii" and also between points "Fi" and "Fii." The compression band formed by the first portion 104B and the second portion 104F may traverse and encircle the abdominis muscles and spine, and may behave like a selectively elastic corset. The first portion 104B of the waist band that extends around the back of the wearer's waist is preferably made of a high compression material. Where the therapeutic shirt 101 is to be worn by an overweight wearer, the second portion 104F of the waist band that extends around the front of the wearer's waist is preferably made of a medium compression material. Where the therapeutic shirt 101 is constructed to be worn by a pregnant woman, the second portion 104F of the waist band that extends around the front of the wearer's waist is preferably made of a low compression material, so that it may have more give to accommodate the woman's physique as the fetus grows and her belly correspondingly grows larger. The first portion 104B and second portion 104F of the waist band and the shoulder band 103 in combination with elasticity of the base shirt 102 cooperate to straighten the wearer's spine and improve his/her posture. This aspect is further enhanced by the following third aspect, which is particularly useful for a very overweight wearer.

Third, a first connector band 105A and a second connector band 105B may be secured to the back side of the base shirt 102. A first end of the first band 105A may be fixedly secured to the top of the first portion 104B of the waist band, approximately midway between the mid-plane of the base shirt 102 and the left side of the shirt (i.e., point "D"). The first band 105A may extend generally towards the top of the shirt, and its second end, upon reaching the band 103, may be fixedly secured thereto, as seen in FIG. 2. A first end of the second band 105B may be fixedly secured to the top of the first portion 104B of the waist band, approximately midway between the mid-plane of the base shirt 102 and the left side of the shirt (i.e., point "E"). The second band 105B may extend generally towards the top of the shirt, and its second end, upon reaching the band 103, may be fixedly secured thereto. The first band 105A and the second band 105B are each preferably made of a high compression material.

Securing of each of the high compression first band 105A and high compression second band 105B between the top of the first portion 104B of the waist band and the high compression band 103 serves to maintain better alignment of the spine.

In one embodiment, for a small sized therapeutic shirt 101, the waist band may be between about 1 inch and about 2 inches wide, and in another embodiment the waist band may be between 2 inches and 4 inches wide, and in yet another embodiment the waist band may be between 4 inches and six inches wide, and in other embodiments, a combination of such ranges or other ranges may be used for the width.

Also, in one embodiment, for a small sized therapeutic shirt 101, each of the shoulder band 103 and the bands 105A and 105B may each be between 0.25 inches and 2.0 inches wide, and in another embodiment each of the shoulder band 103 and the bands 105A and 105B may each more preferably be between 0.5 inches and 1.5 inches wide, and in yet another embodiment, each of the shoulder band 103 and the bands 105A and 105B may each more preferably be between 0.75 inches and 1.25 inches wide. In other embodiments, different widths may be used.

To achieve the desired effects for the therapeutic shirt 101, the elastic material 102 that is used to faun the base shirt 102 may provide a first compression level that is intended to conform to the wearer's body. In one embodiment this elastic material may exhibit a compression pressure in the range of 2 mm Hg to 5 mm Hg, and in another embodiment the elastic material may exhibit a compression pressure in the range of 5 mm Hg to 8 mm Hg, and in yet another embodiment the elastic material may exhibit a compression pressure in the range of 8 mm Hg to 11 mm Hg, and in another embodiment the elastic material may exhibit a compression pressure in the range of 11 mm Hg to 16 mm Hg, and in other embodiments other ranges or a combinations of those ranges may instead be used.

The shoulder band 103 (and also the first and second connector bands 105A and 105B where utilized) is/are made of a high compression material to apply a second level of compression, being higher than the first level of compression. In one embodiment this high compression material may be formed to exhibit a compression pressure in the range of 35 mm Hg to 45 mm Hg, and in another embodiment the high compression material may exhibit a compression pressure in the range of 45 mm Hg to 55 mm Hg, and in yet another embodiment the high compression material may exhibit a compression pressure in the range of 55 mm Hg to 65 mm Hg, and in another embodiment the high compression material may exhibit a compression pressure in the range of 65 mm Hg to 88 mm Hg, and in other embodiments other ranges or a combinations of those ranges may instead be used.

The first portion 104B of the waist band that extends around the back of the wearer's waist that is also preferably made of a high compression material (i.e., it provides the second level of compression), and may exhibit a compression pressure in the above noted ranges for the various different embodiments, the same as the shoulder band 103.

The second portion 104F of the waist band that extends around the front of the wearer's waist is preferably made of a low compression material or medium compression material to provide a third level of compression. For the therapeutic shirt 101 constructed to be worn by an overweight person, the third level of compression for the second portion 104F of the waist band is provided through the use of a medium compression material that in one embodiment may exhibit a compression pressure in the range of 25 mm Hg to 28 mm Hg, and in another embodiment may exhibit a compression pressure in the range of 28 mm Hg to 31 mm Hg, and in another embodiment may exhibit a compression pressure in the range of 31 mm Hg to 35 mm Hg, and in other embodiments other ranges or a combinations of those ranges may instead be used. For the therapeutic shirt 101 constructed to be worn by a pregnant woman, the third level of compression for the second portion 104F of the waist band is provided through the use of a low compression material that in one embodiment may exhibit a compression pressure in the range of 15 mm Hg to 18 mm Hg, and in another embodiment may exhibit a compression pressure in the range of 18 mm Hg to 21 mm Hg, and in another embodiment may exhibit a compression pressure in the range of 21 mm Hg to 25 mm Hg, and in other embodiments other ranges or a combinations of those ranges may instead be used. The second portion 104F of the waist band that extends around the front of the women's waist being made of a low compression material to provide that particular third level of compression is so configured to more easily conform to the women's waist and belly that houses a fetus, than does the medium compression material for the overweight wearer whose belly is mostly composed of fat.

Figure 9:
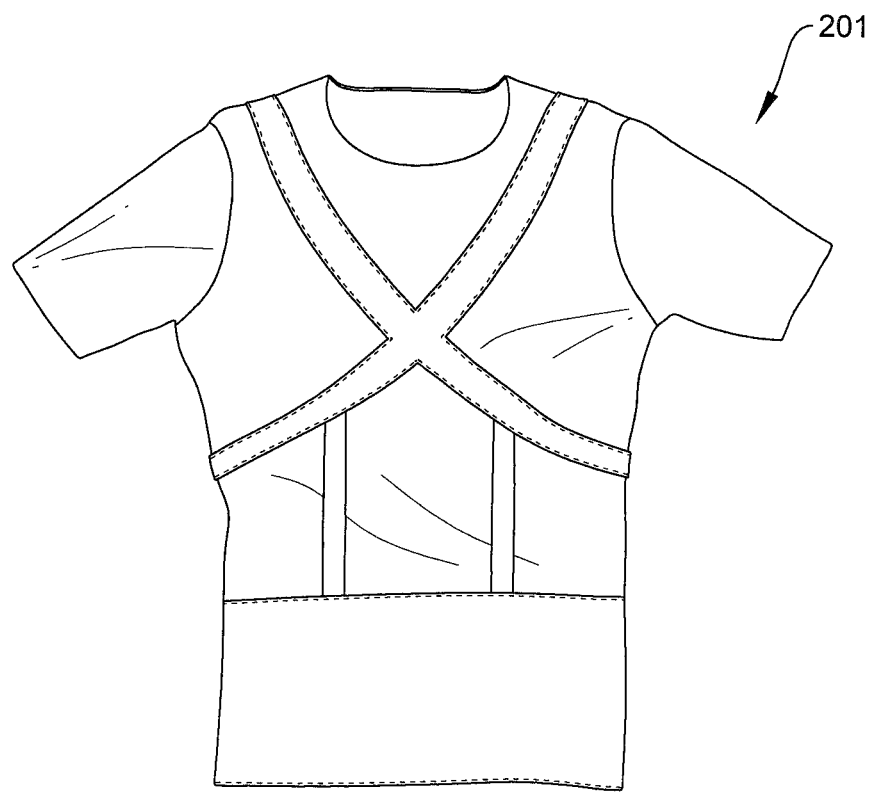
FIG. 9 is a rear view of the therapeutic shirt shown in FIG. 8.
Figure 10:
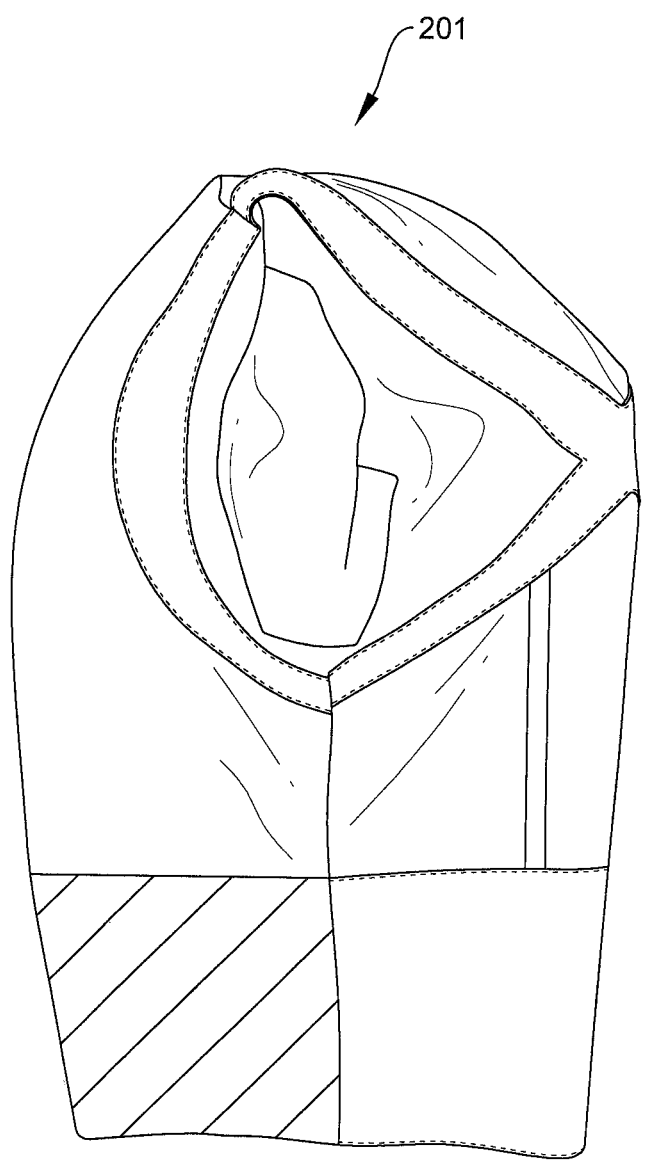
FIG. 10 is a side view of the therapeutic shirt shown in FIG. 8.
Figure 11:
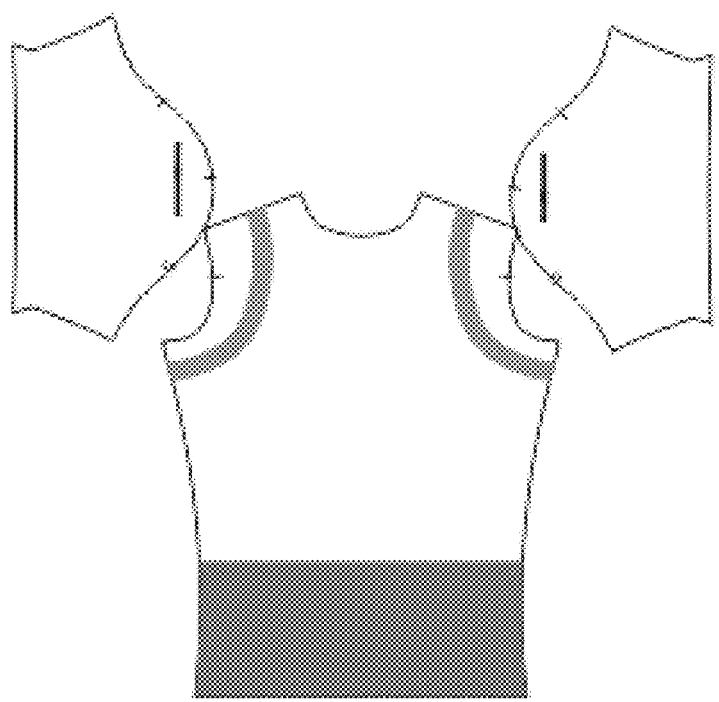
FIG. 11 and FIG. 12 are views of the flat patterns for the front side and sleeves, and for the rear side of the therapeutic shirt formed similar to the therapeutic shirt of FIG. 8, but also having a compression fabric at the front bottom portion of the shirt.
Figure 12:
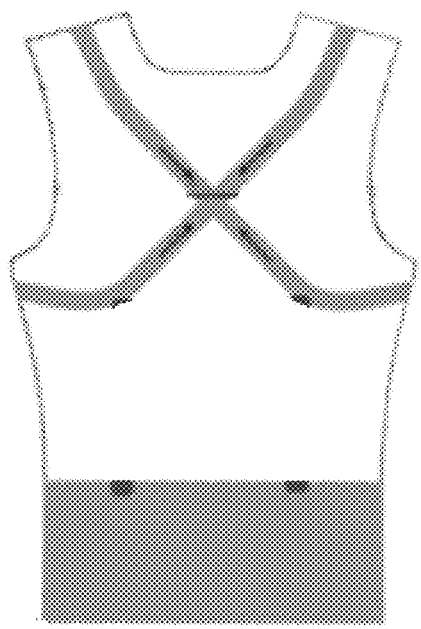

FIGS. 8-12 illustrate views of a second therapeutic shirt 201 that is formed the same as therapeutic shirt 101 except that it does not have the high compression first band 105A and second band 105B (compare FIG. 9 with FIG. 2).

Figure 13:
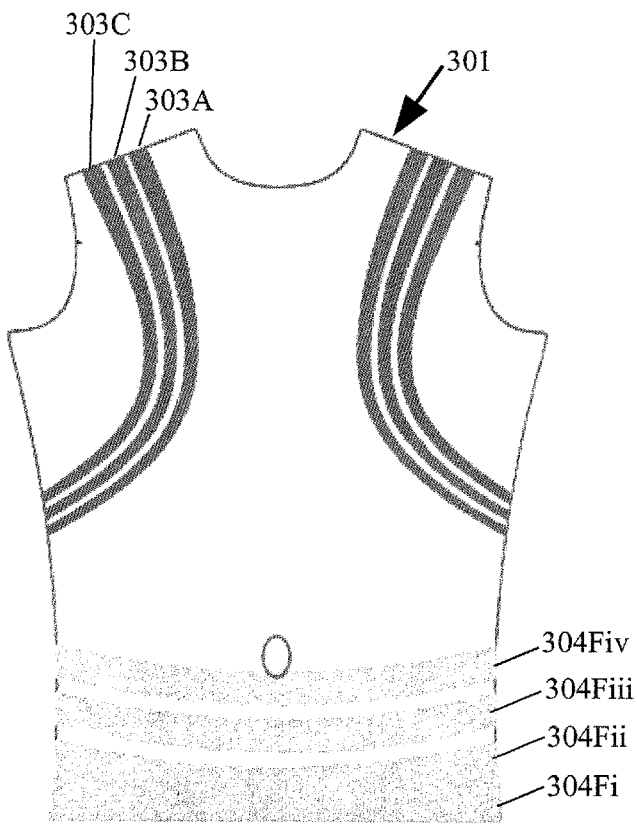
FIG. 13 is a front view of third embodiment of a therapeutic shirt particularly configured for use by an overweight person.
Figure 14:
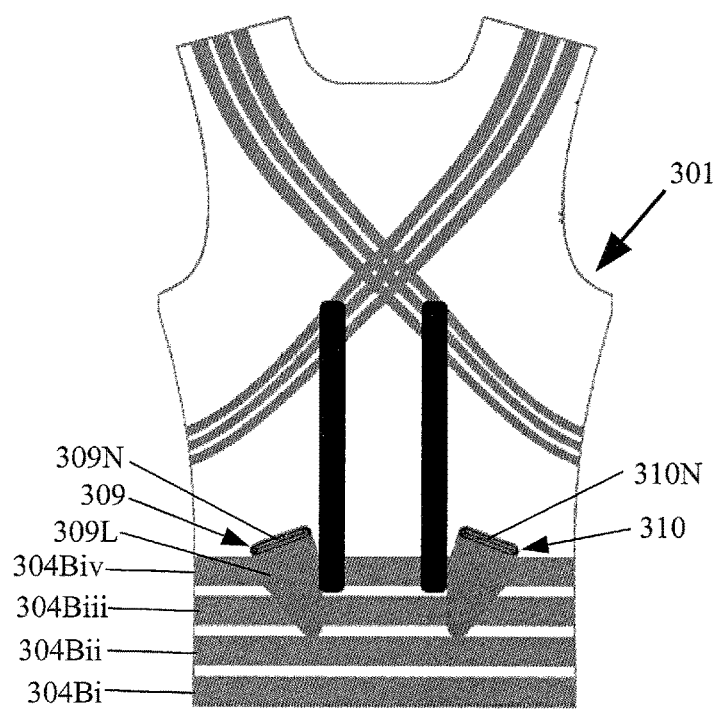
FIG. 14 is a rear view of the therapeutic shirt of FIG. 13, showing the high compression regions located thereon, and pockets positioned on the rear side of the shirt to receive hot/cold packs.

FIGS. 13-14 illustrate views of a third therapeutic shirt 301 which may be formed the same as either therapeutic shirt 101 or therapeutic shirt 201, except that the single high compression band 103 of shirt 101 may be separated into three (or even four) smaller bands (e.g., bands 303A, 303B, and 303C) for the therapeutic shirt 301, which may provide greater comfort and a better fit for the wearer, while still providing support as previously described. Also, the single waist band of shirt 101 that is made up of sections 104B and 104F may instead be separated into a plurality (e.g., three or four) narrower waist bands for therapeutic shirt 301, each of which may comparably be formed into two sections, being the four back sections 304Bi, 304Bii, 304Biii, and 304Biv that may respectively connect to the four front sections 304Fi, 304Fii, 304Fiii, and 304Fiv. Note that in another embodiment two of the front sections (e.g., 304Fi and 304Fii) may be merged into a single compression band so that there may be three bands.

Also, in one embodiment, for a small sized therapeutic shirt 301 (or for shirt 401 described hereinafter), each of the multiple narrow waist bands may be between 0.25 inches and 2.0 inches wide, and in another embodiment that width may more preferably range between 0.50 inches and 1.5 inches wide, and in yet another embodiment that width may most preferably be in the range between 0.75 inches and 1.25 inches. In other embodiments, a combination of those width ranges or other width ranges may be used instead.

The third therapeutic shirt 301, as well as the therapeutic shirt 101 and the therapeutic shirt 201, may also have a pair of pockets formed in the back (see e.g., pockets 309/310 for the third therapeutic shirt 301 in FIG. 14), which pockets may be configured to receive hot/cold packs to treat the back (e.g., to reduce the effects of, or the likelihood of developing, sciatica). In one embodiment the respective openings for each of the pockets (e.g., openings 309N/310N for pockets 309/310) are preferably positioned above the uppermost extent of high compression material of the waist band (e.g., above the uppermost extent of band 304Biv for the third therapeutic shirt 301). The openings for each of the pockets may be reinforced in any suitable manner, including, but not limited to, the use of rivets, or a grommet (metal, rubber, etc.), or an eyelet, or other reinforcing materials, including, but not limited to, stitching, a printed silicon, and plastic material.

Figure 24:
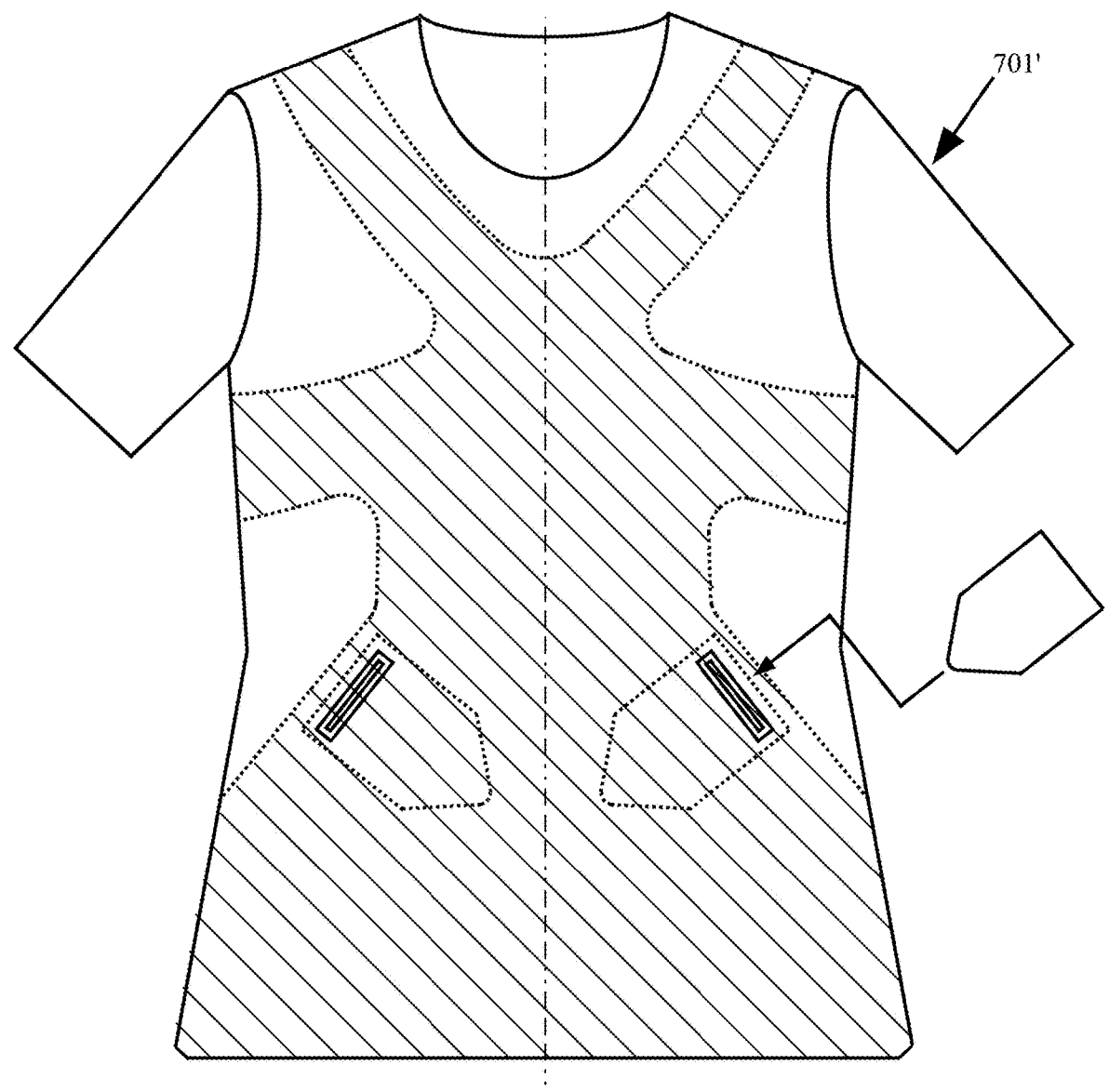

In one embodiment the interior of each of the pockets 309/310 is positioned above each of the layers of high compression material, and is therefore disposed farthest away from the wearer's skin surface, and would require material to be added above the outermost high compression layer of material to form the pocket, which added material may also be the same high compression material or a basic liner material 309L. In another embodiment each of the pockets 309/310 may be positioned between the layers of high compression material (i.e., between the innermost layer and the middle layer, or between the middle layer and the outermost layer). In yet another embodiment, which offers several advantages, each of the pockets 309/310 may be positioned beneath each of the multiple layers of high compression material, and therefore is disposed closest to the wearer's skin surface, which would also require material to be added beneath the innermost high compression layer of material, i.e., a liner material.

Where the pockets are positioned beneath the innermost layer of high compression material, or positioned between the innermost layer and the middle layer, or between the middle layer and the outermost layer, the high compression material that forms the individual bands on the back of the shirt (304Bi, 304Bii, 304Biii, and 304Biv) may extend locally to overlie the full extent of the pockets 309/310, and may thus extend to connect portions of the band 304Biv with band 304Biii, and portions of band 304Biii with band 304Bii, as seen in FIG. 24, which high compression areas may serve to force the hot/cold packs into contact with the wearer's back. In this arrangement, the high compression areas over the pockets also serves as insulation for the pockets, which results in far greater thermal efficiency and permits the use of a hot/cold pack weighing around only 18 grams, but which has the equivalent efficiency of a hot/cold pack weighing nearly ten times the weight, also thereby promoting greater longevity for the heat provide therefrom, due to the high compression layers acting as a thermal barrier. The pockets 309/310 may also be configured to terminate in a point, and the hot/cold packs may be similarly shaped to assist in the insertion of the hot/cold packs into the pockets while the shirt is being worn.

Hot and cold packs are known in the art, as shown for example by the following U.S. Pat. No. 2,907,173 to Robbins; U.S. Pat. No. 3,175,558 to Caillouette; U.S. Pat. No. 3,342,324 to Piazze; U.S. Pat. No. 3,542,032 to Spencer; U.S. Pat. No. 3,804,077 to Williams; U.S. Pat. No. 4,462,224 to Dunshee; U.S. Pat. No. 5,792,213 to Bowen; U.S. Pat. No. 3,889,684 to Lebold; U.S. Pat. No. 4,462,224 to Dunshee; U.S. Pat. No. 4,700,706 to Munch; U.S. Pat. No. 5,190,033 to Johnson; and U.S. Pat. No. 5,843,145 to Brink.

Figure 15:
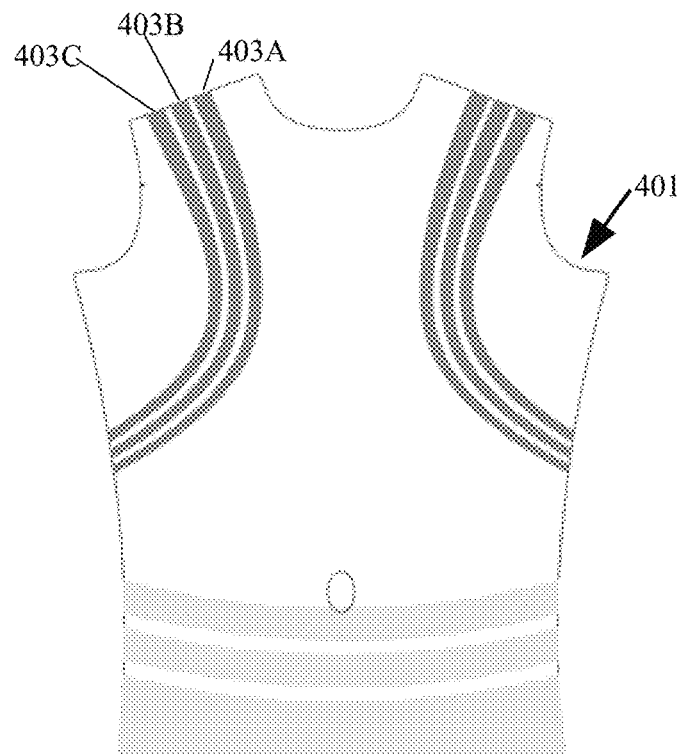
FIG. 15 is a front view of fourth embodiment of a therapeutic shirt being particularly configured for use by a pregnant woman.
Figure 16:
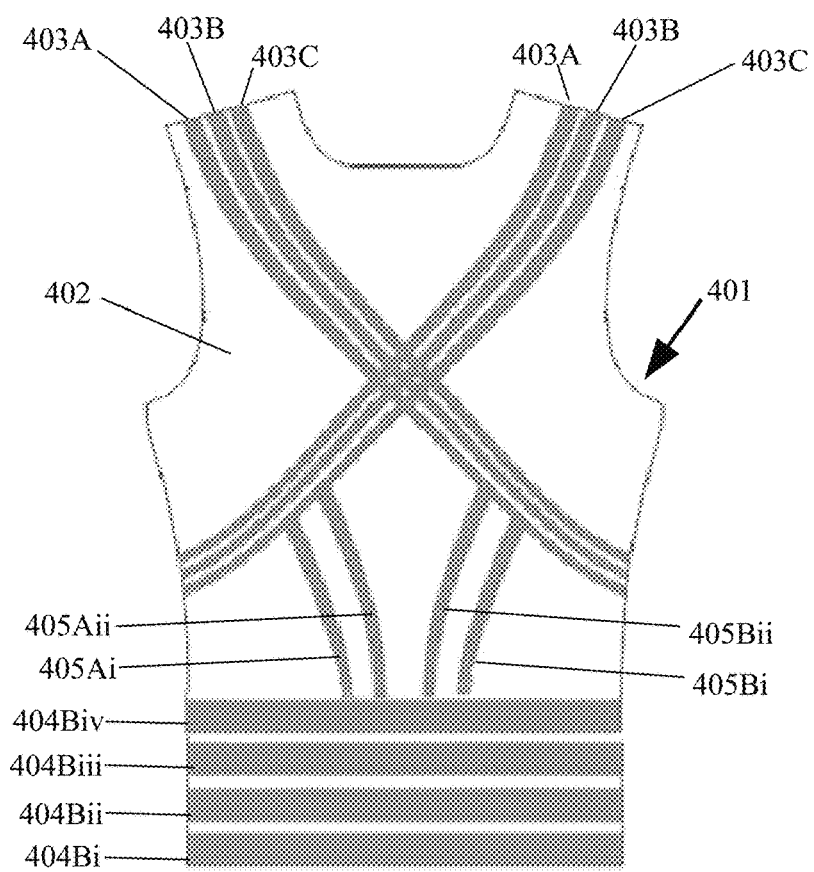
FIG. 16 is a rear view of the therapeutic shirt of FIG. 15.

FIGS. 15-16 illustrate views of a fourth embodiment—therapeutic shirt 401 which may be formed the same as therapeutic shirt 301, having three or four waist band sections on the front side connecting to waist band sections on the back side (e.g., bands 404Bi, 404Bii, 404Biii, and 404Biv) of the base shirt 402, and three (or even four) smaller high compression bands (e.g., bands 403A, 403B, and 403C) that may encircle the shoulders and cross at the back. In addition, there may be one or two high compression bands that connect between band 403C and band 404Biv on the left side of the back (e.g., bands 405Ai and/or 405Aii), and there may be one or two high compression bands that connect between band 403A and band 404Biv on the right side of the back (e.g., bands 405Bi and/or 405Bii). In other embodiments, the bands 405Ai and 405Aii, and bands 405Bi and 405Bii may each extend over and connect to each of the bands 403A, 403B, and 403C.

Figure 17:
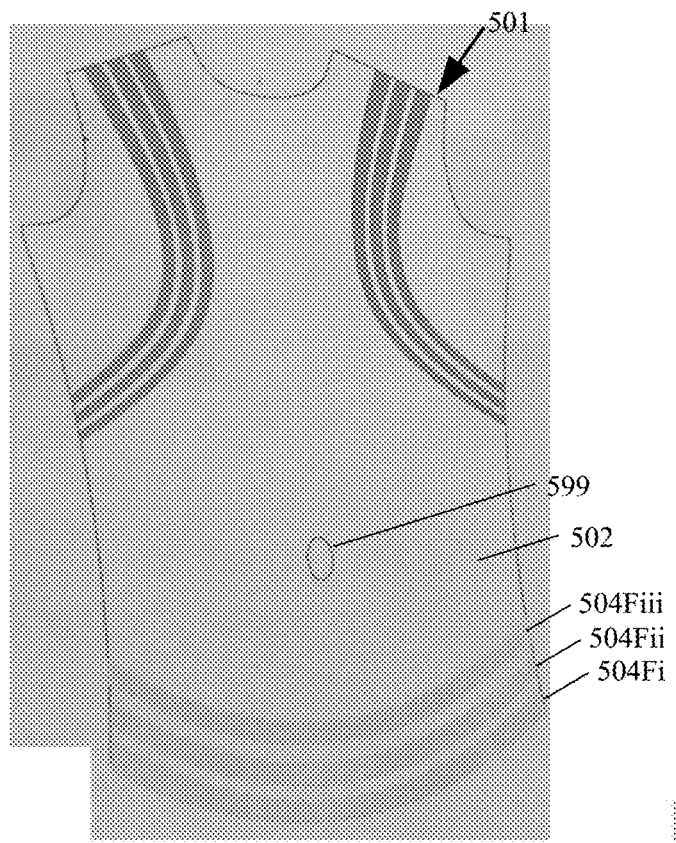
FIGS. 17-18 are a front view and a rear perspective view, respectively, of a fifth embodiment of a therapeutic shirt being particularly configured for use by a pregnant woman.
Figure 18:
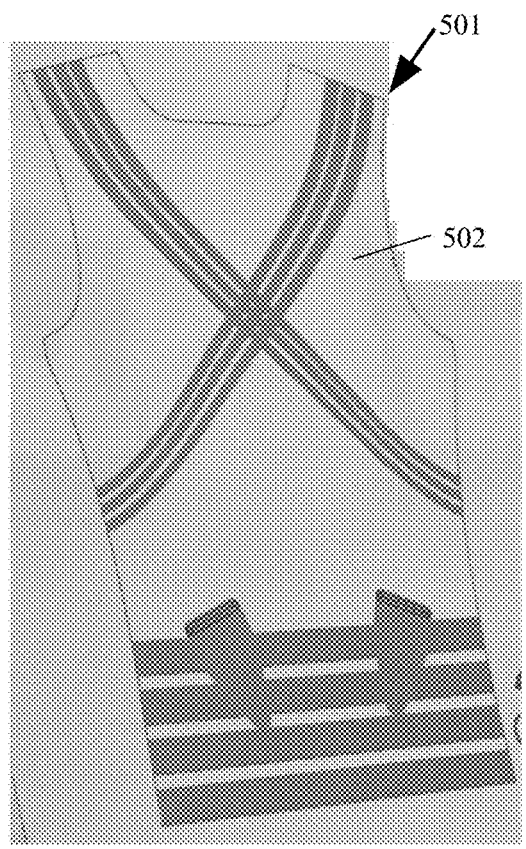

FIGS. 17-18 illustrate views of a fifth embodiment—therapeutic shirt 501 which may be formed the same as therapeutic shirt 301, except that the narrow waist bands on the front (e.g., bands 504Fi, 504Fii, and 504Fiii) of the base shirt 502 may be curved downwardly well below the wearer's belly button 599, as shown in FIG. 17, rather than being straight, to provide greater comfort for the growing belly of a pregnant woman.

Figure 19:
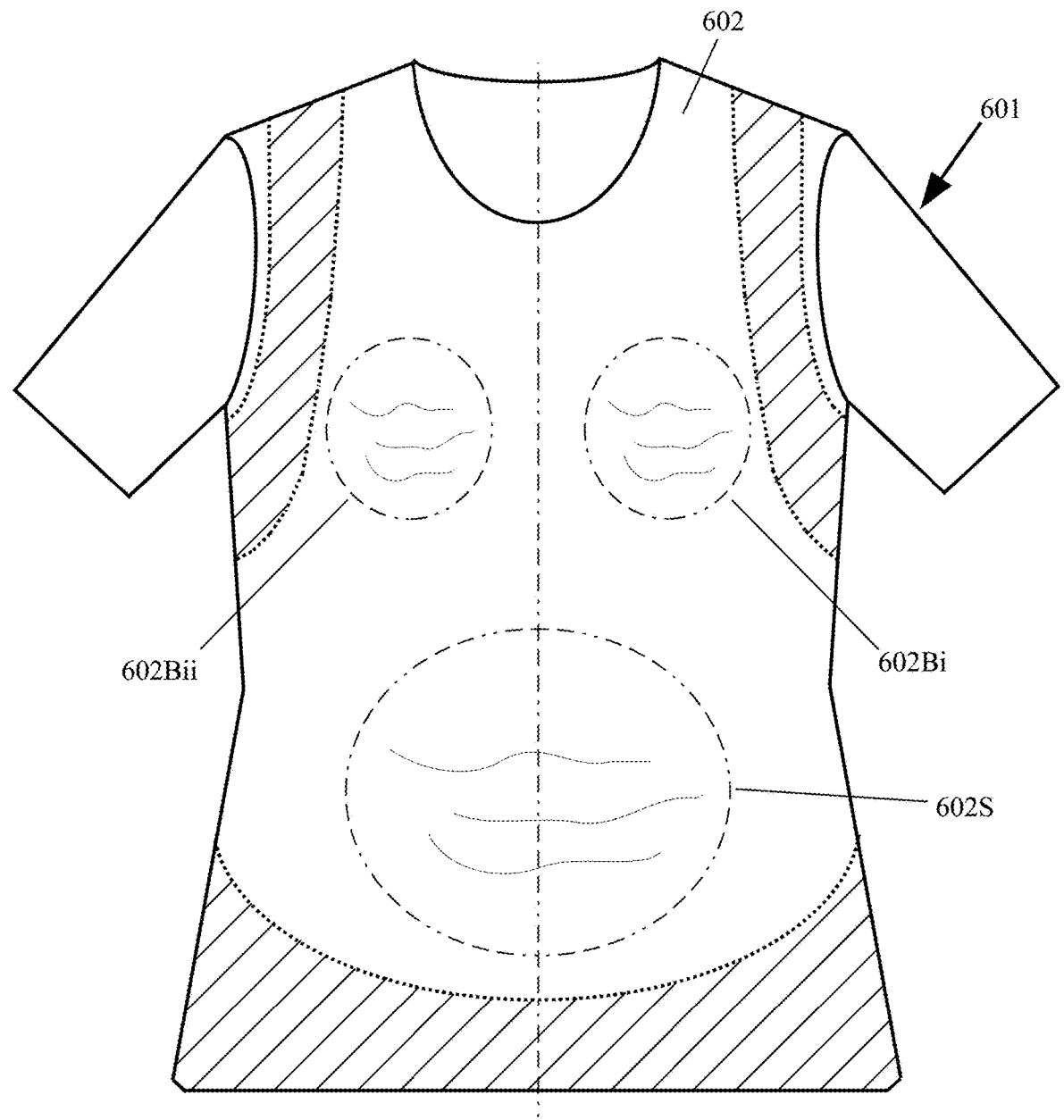
FIGS. 19-20 are a front view and a rear view, respectively, of a sixth embodiment of a therapeutic shirt being particularly configured for use by a pregnant woman.

FIG. 19 illustrates a front view of a sixth therapeutic shirt 601 which is also particularly configured for use by a pregnant woman, and which may also be formed similar to the therapeutic shirt 301, but with several differences that are shown within FIGS. 19-22. The base shirt 602 may be tapered to better conform to a woman's hour-glass shaped figure. The uniformly elastic material of the base shirt 602 may also be interrupted at three locations—at two upper locations 602Bi and 602Bii, and one lower location 602S. The two upper locations 602Bi and 602Bii may be formed to accommodate the woman's breasts, and at those locations the elastic material may be locally deformed to lose some of its elasticity, and may have permanent stretch formed therein so as to provide for a little looser fit around the woman's breasts. In another embodiment the elastic material in those two regions may be replaced by a different material that may be generously supplied therein and may be gathered, and which may or may not be elastic material, to similarly accommodate the woman's breasts. A non-stretch reinforcement material may be positioned around the periphery of those two regions to resist the pull of the elastic stretch material, which may include, but is not limited to, a different type of fabric, or a hard plastic ring. The one lower region 602S, may be similarly formed, but may be sized and positioned to accommodate the woman's baby bump.

The first band 605A and second band 605B that may be secured to the back side of the base shirt 602 may be wider to provide greater support than the bands 105A and 105B of shirt 101 or the similar bands for shirt 301. The first band 605A and second band 605B may also transition much more gradually into the back portion 604B of the waist band.

Figure 21:
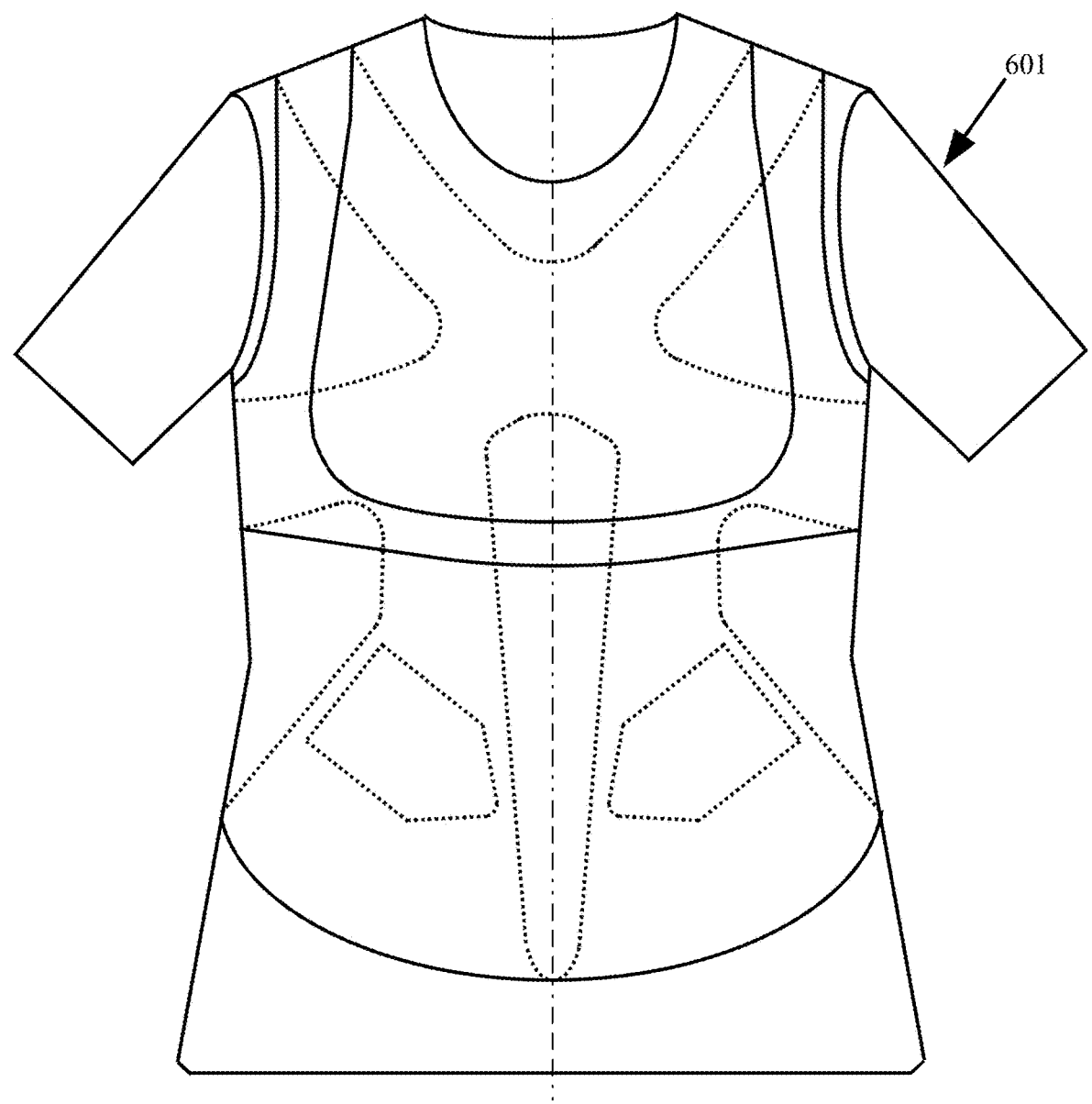
FIGS. 21-22 are front and rear views of the therapeutic shirt of FIGS. 19-20, but shown with the shirt turned inside out.
Figure 22:
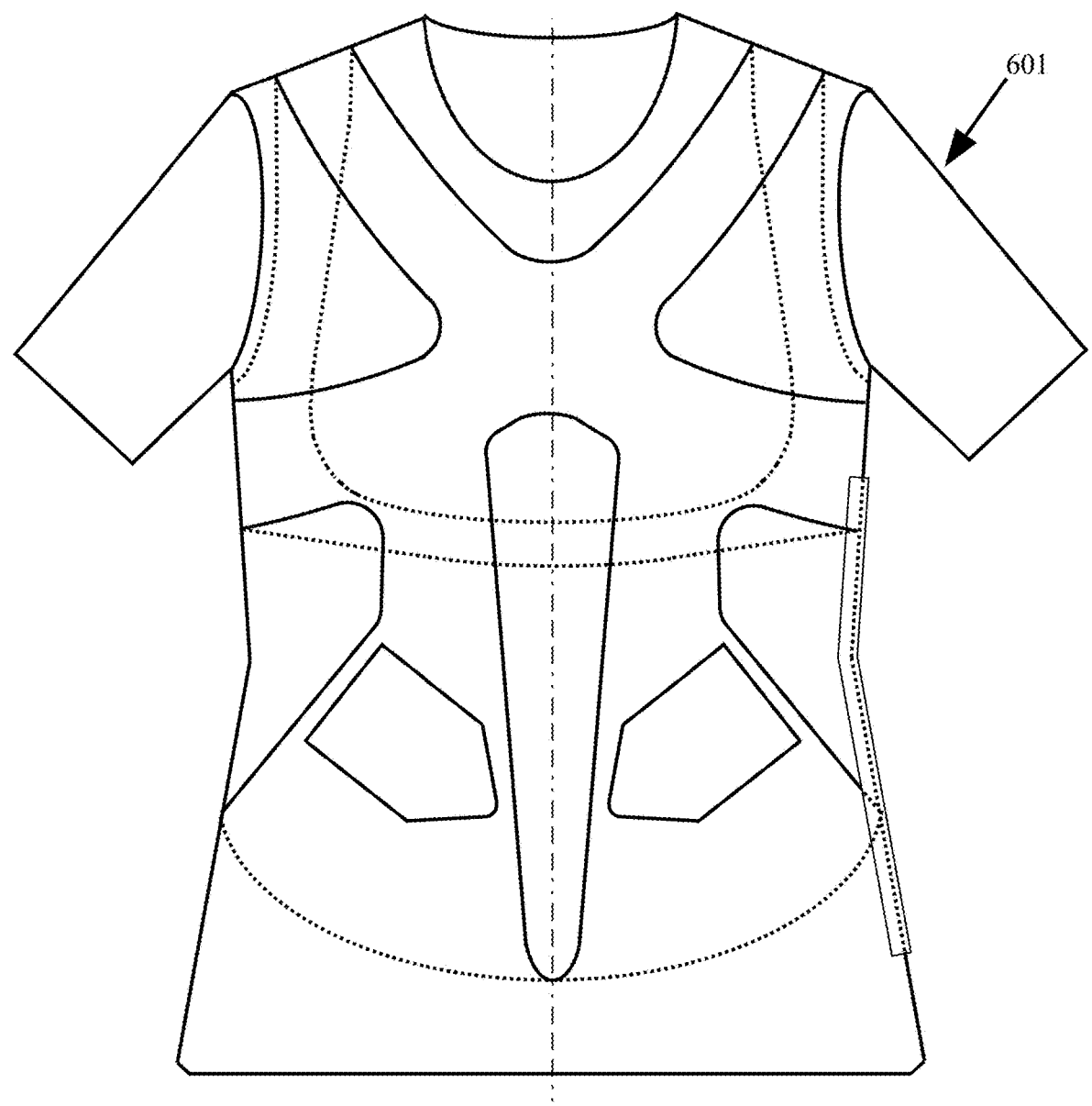

As seen in the views of FIGS. 21-22, in which the therapeutic shirt 601 is illustrated to be inside out, the high compression material secured to each of the front side and rear side of the base shirt 602 may be formed of one seamless piece of material, as the connections/transitions between the high compression regions on the front and rear may be continuous. (Note that the high compression materials may be secured to the shirt on the outside, or secured on its inside). For ease of manufacturing the therapeutic shirt 601, the base shirt 602 may be formed of at least two pieces of elastic material that may be seamed at the side (the sleeves may be formed of separate material portions); also, the high compression material for the regions on the front may be formed of one piece, while the high compression material for the regions on the rear may also be one piece, which two pieces of high compression material may similarly be joined at the sides of the shirt.

Also, to provide for easier ingress and egress by the pregnant woman into and out from the therapeutic shirt 601, at least one of the sides may be formed to include a zipper 610. The zipper 610 may extend from beneath the sleeve towards the bottom of the shirt, but terminates at a point above the bottom of the shirt, so that a portion of the front and back portion 604B of the waist band is continuous thereat. In another embodiment, a zipper 610 may utilized on each of the two sides. Once the woman has donned the therapeutic shirt 601, the zipper(s) may be zipped up to provide the designed high compression support.

Figure 23:
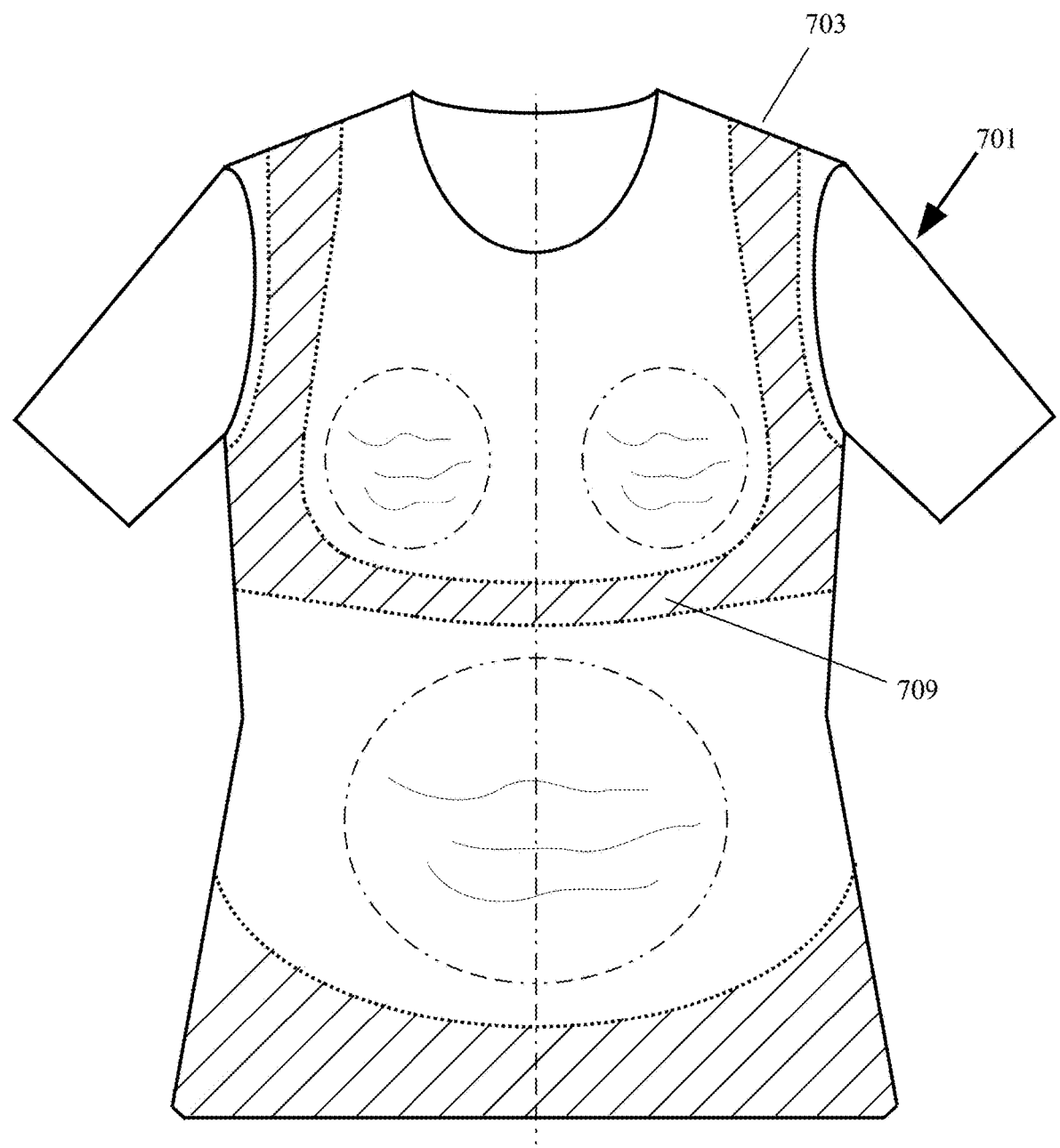
FIGS. 23-24 are a front view and a rear view, respectively, of a seventh embodiment of a therapeutic shirt being particularly configured for use by a pregnant woman.

FIG. 23 is a front view of a therapeutic shirt 701 that is an alternate embodiment of the shirt 601 shown in FIG. 19, in which the high compression material that formed the shoulder band 603 that loops around the shoulders of shirt 601 are formed as a band 703 that is coupled together across the front of the wearer beneath the breasts with a connecting strip 709 of high compression material.

Figure 20:
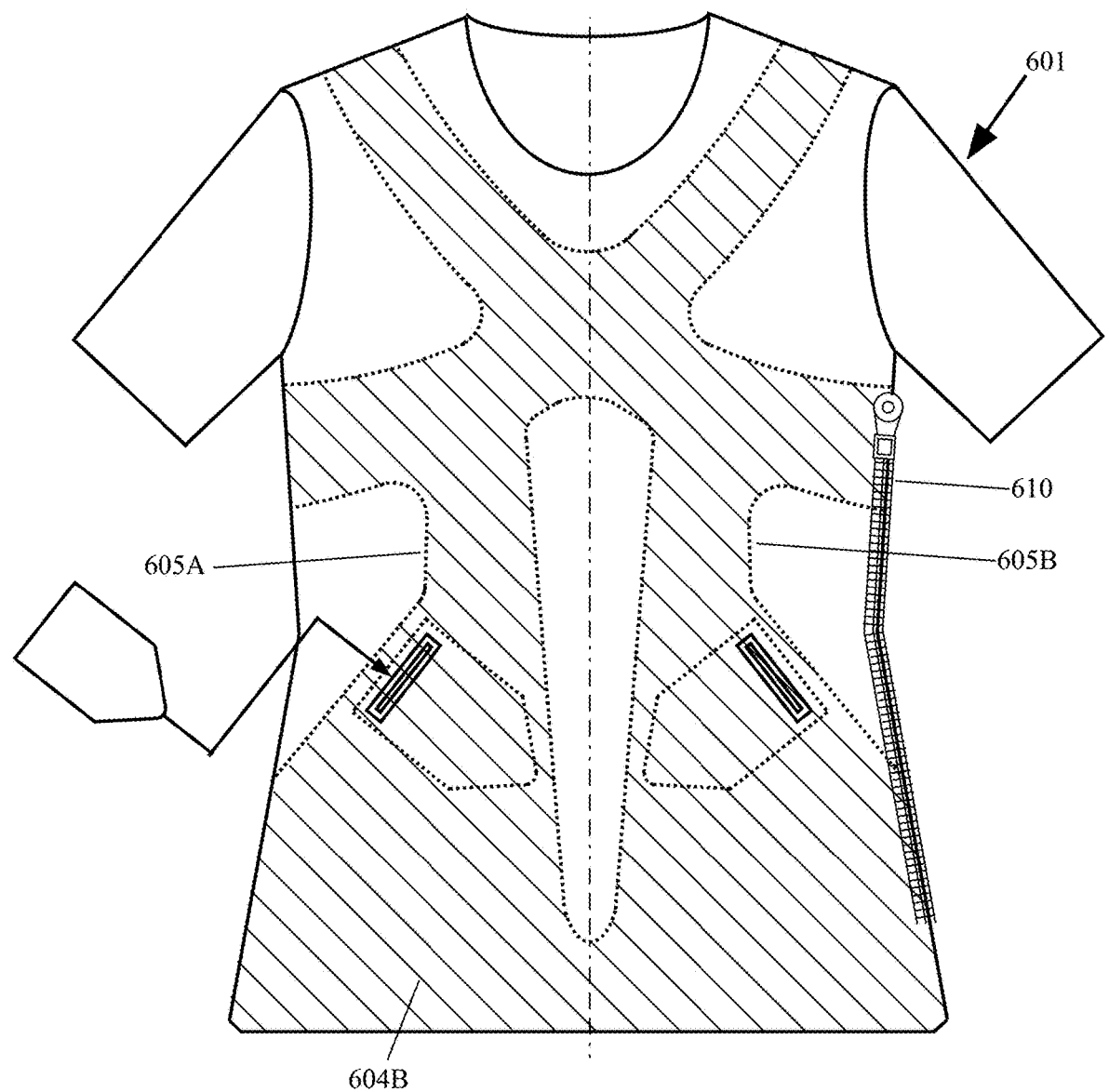

FIG. 24 is a rear view of a therapeutic shirt 701' that is an alternate embodiment of the shirt 601 as seen in FIG. 20, in which the first band 605A and second band 605B on the back of shirt 601 merge together on the back of shirt.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A posture support garment for improving the posture of a wearer, said posture support garment comprising: a shirt configured to envelop at least a portion of the wearer's torso and the wearer's shoulders, said shirt comprising an elastic material configured to apply a first level of compression; a shoulder band, said shoulder band fixedly secured to said shirt by being stitched to said shirt, and configured to encircle a left shoulder region and a right shoulder region of said shirt and to crisscross at an upper central region of a back of said shirt, said shoulder band comprising a first compression material configured to apply a second level of compression; wherein said shoulder band is configured to cross over said right shoulder region of said shirt, travel down a right chest region of a front of said shirt and curve backwardly around a right side of said shirt and traverse across said back of said shirt diagonally and upwardly towards said left shoulder region, cross over said left shoulder region of said shirt, travel down a left chest region of said front of said shirt and curve backwardly around a left side of said shirt and traverse across said back of said shirt diagonally and upwardly towards said right shoulder region; wherein said shoulder band at said traverse across said back of said shirt diagonally and upwardly towards said left shoulder region crisscrosses and interconnects with said shoulder band at said traverse across said back of said shirt diagonally and upwardly towards said right shoulder region, to form a figure eight shape; a waist band, said waist band positioned distally from said shoulder band and configured to encircle the wearer's waist, said waist band comprising a first portion and a second portion formed into a circumferential band; said second portion of said waist band configured to extend around a front of the wearer's waist and comprises a second compression material configured to apply a third level of compression; said first portion of said waist band being configured to extend around a back of the wearer's waist and comprises said first compression material configured to apply said second level of compression; wherein at least a portion of said waistband is secured onto said shirt by being stitched to said shirt; and wherein said third level of compression is less than said second level of compression; and a first connector band, said first connector band secured to said back of said shirt, and configured to have a first end secured to a top of said first portion of said waist band, and a second end secured to said shoulder band at a position between where said shoulder band curves around said right side of said shirt and said crisscross at said upper central region of said back of said shirt; a second connector band, said second connector band secured to said back of said shirt, and configured to have a first end secured to said top of said first portion of said waist band, and a second end secured to said shoulder band at a position between where said shoulder band curves around said left side of said shirt and said crisscross at said upper central region of said back of said shirt; wherein said shirt has a central axis that extends from a top of said shirt to a bottom of said shirt, said shirt being symmetrical about said central axis: and wherein each of said first connector band and said second connector band are parallel to said central axis.

2. The posture support garment according to claim 1, wherein said crisscross of said shoulder band at said back of said shirt is formed as a single continuous member to create said crisscrossed interconnection.

3. The posture support garment according to claim 1, wherein said traverse across said back of said shirt diagonally and upwardly towards said left shoulder crosses over and is fixedly secured to said traverse across said back of said shirt diagonally and upwardly towards said right shoulder, to create said crisscrossed interconnection.

4. The posture support garment according to claim 1, wherein when the wearer is a pregnant wearer, said first compression material of said waist band comprises a high compression material, and said second compression material of said waist band comprises a low compression material.

5. The posture support garment according to claim 1, wherein when the wearer is an overweight wearer, said first compression material comprises a high compression material, and said second compression material comprises a medium compression material.

6. The posture support garment according to claim 5, wherein said shirt is formed of a single layer of said elastic material; and
wherein said elastic material is selected from the group consisting of: a spandex, a polyester blend, and a bamboo blend.

7. The posture support garment according to claim 6, wherein said medium compression material and said high compression material are each formed of a plurality of layers of compression materials selected from the group consisting of: a thermoplastic elastomer (TPE), and a polyurethane.

8. The posture support garment according to claim 1, wherein said shoulder band is formed of one continuous piece of said first compression material.

9. A posture support garment configured to improve the posture of a wearer, said posture support garment comprising:
a shirt configured to envelop at least a portion of the wearer's torso and the wearer's shoulders, said shirt comprising an elastic material configured to apply a first level of compression;
a shoulder band, said shoulder band fixedly secured to said shirt by being stitched to said shirt, and configured to encircle a left shoulder region and a right shoulder region of said shirt and to crisscross at an upper central region of a back of said shirt, said shoulder band comprising a first compression material configured to apply a second level of compression;
wherein said shoulder band is configured to cross over said right shoulder region of said shirt, travel down a right chest region of a front of said shirt and curve backwardly around a right side of said shirt and traverse across said back of said shirt diagonally and upwardly towards said left shoulder region, cross over said left shoulder region of said shirt, travel down a left chest region of said front of said shirt and curve backwardly around a left side of said shirt and traverse across said back of said shirt diagonally and upwardly towards said right shoulder region;
wherein said shoulder band at said traverse across said back of said shirt diagonally and upwardly towards said left shoulder region crisscrosses and interconnects with said shoulder band at said traverse across said back of said shirt diagonally and upwardly towards said right shoulder region, to form a figure eight shape;
a waist band, said waist band positioned distally from said shoulder band and configured to encircle the wearer's waist, said waist band comprising a first portion and a second portion formed into a circumferential band; said second portion of said waist band configured to extend around a front of the wearer's waist and comprises a second compression material configured to apply a third level of compression; said first portion of said waist band being configured to extend around a back of the wearer's waist and comprises said first compression material configured to apply said second level of compression; wherein at least a portion of said waistband is secured onto said shirt being stitched to said shirt;
wherein said third level of compression is less than said second level of compression;
a first connector band, said first connector band secured to said back of said shirt, and configured to have a first end secured to a top of said first portion of said waist band, and a second end secured to said shoulder band at a position between where said shoulder band curves around said right side of said shirt and said crisscross at said upper central region of said back of said shirt;
a second connector band, said second connector band secured to said back of said shirt, and configured to have a first end secured to said top of said first portion of said waist band, and a second end secured to said shoulder band at a position between where said shoulder band curves around said left side of said shirt and said crisscross at said upper central region of said back of said shirt;
wherein said shirt has a central axis that extends from a top of said shirt to a bottom of said shirt, said shirt being symmetrical about said central axis; and
wherein each of said first connector band and said second connector band are parallel to said central axis;
wherein said crisscross of said shoulder band at said back of said shirt is formed as a single continuous member to create said crisscrossed interconnection; and
wherein said traverse across said back of said shirt diagonally and upwardly towards said left shoulder crosses over and is fixedly secured to said traverse across said back of said shirt diagonally and upwardly towards said right shoulder, to create said crisscrossed interconnection.

10. The posture support garment according to claim 9, wherein when the wearer is a pregnant wearer, said first compression material of said waist band comprises a high compression material, and said second compression material of said waist band comprises a low compression material.

11. The posture support garment according to claim 9, wherein when the wearer is an overweight wearer, said first compression material comprises a high compression material, and said second compression material comprises a medium compression material.

\* \* \* \* \*